(12) United States Patent
Kay et al.

(10) Patent No.: US 9,097,721 B2
(45) Date of Patent: Aug. 4, 2015

(54) COMPOSITIONS COMPRISING ENGINEERED PHOSPHOTHREONINE AFFINITY REAGENTS, METHODS OF MAKING, AND METHODS OF USE

(71) Applicant: The Board of Trustees of the University of Illinois, Urbana, IL (US)

(72) Inventors: Brian K. Kay, Chicago, IL (US); Kritika Pershad, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 13/781,079

(22) Filed: Feb. 28, 2013

(65) Prior Publication Data
US 2013/0225434 A1 Aug. 29, 2013

Related U.S. Application Data

(60) Provisional application No. 61/726,438, filed on Nov. 14, 2012, provisional application No. 61/604,930, filed on Feb. 29, 2012.

(51) Int. Cl.
*C40B 40/10* (2006.01)
*G01N 33/68* (2006.01)

(52) U.S. Cl.
CPC ............... *G01N 33/68* (2013.01); *C40B 40/10* (2013.01)

(58) Field of Classification Search
None
See application file for complete search history.

(56) References Cited

U.S. PATENT DOCUMENTS 6,794,128 B2 9/2004 Marks

OTHER PUBLICATIONS

Bangalore L et al., "Antiserum raised against a synthetic phosphotyrosine-containing peptide selectively recognizes p185neu/erbB-2 and the epidermal growth factor receptor", Proc Natl Acad Sci USA, 2001;89:11637-41.
Byeon IJ et al., "Solution structure of the yeast Rad53 FHA2 complexed with a phosphothreonine peptide pTXXL: comparison with the structures of FHA2-pYXL and FHA1-pTXXD complexes", J Mol Biol. 2001:314:577-88.
Bridges D et al., "14-3-3 proteins: a number of functions for a numbered protein", Sci STKE. 2005;2005:re10.
Brizzard B. et al., "Epitope tagging of recombinant proteins", Curr Protoc Neurosci, 2001:Ch. 5, Unit 5.8.
Cadwell RC et al., "Mutagenic PCR", PCR Methods Appl. 1994;3:S136-40.
Cohen P. "The role of protein phosphorylation in human health and disease." Eur J Biochem. 2001;268:5001-10.
Durocher D. et al., "The FHA domain is a modular phosphopeptide recognition motif", Mol Cell. 1999;4:387-94.
Durocher D. et al., "The molecular basis of FHA domain:phosphopeptide binding specificity and implications for phospho-dependent signaling mechanisms", Mol Cell. 2000;6:1169-82.
Durocher D. et al., "The FHA domain", FEBS Lett. 2002;513:58-66.
Elia AE et al., "The molecular basis for phosphodependent substrate targeting and regulation of Plks by the Polo-box domain", Cell. 2003;115:83-95.
Ernst A. et al., "Rapid evolution of functional complexity in a domain family", Sci Signal. 2009;2:ra50.

(Continued)

*Primary Examiner* — Christian Boesen
(74) *Attorney, Agent, or Firm* — McDonnell Boehnen Hulbert & Berghoff LLP

(57) ABSTRACT

This invention relates to the use of protein scaffolds for producing affinity reagents that are polypeptides that specifically bind to phosphopeptides.

5 Claims, 21 Drawing Sheets

(56) References Cited

OTHER PUBLICATIONS

Giuliani SE et al., "Functional assignment of solute-binding proteins of ABC transporters using a fluorescence-based thermal shift assay", Biochemistry. 2008;47:13974-84.

Gebauer M. et al., "Engineered protein scaffolds as next-generation antibody therapeutics", Curr Opin Chem Biol. 2009;13:245-55.

Haidaris CG et al., "Recombinant human antibody single chain variable fragments reactive with *Candida albicans* surface antigens", J Immunol Methods, 2001;257:185-202.

Jespers L. et al., "Structure of HEL4, a soluble, refoldable human VH single domain with a germ-line scaffold", J. Mol. Biol. 2004;337:893-903.

Jung S. et al., "Selection for improved protein stability by phage display", J Mol Biol. 1999;294:163-80.

Lee H. et al., "Diphosphothreonine-specific interaction between an SQ/TQ cluster and an FHA domain in the Rad53-Dun1 kinase cascade", Mol Cell. 2008;30:767-78.

Li J. et al., "The FHA domain mediates phosphoprotein interactions", J Cell Sci. 2000;113(Pt 23):4143-9.

Li J. et al., "Structural and functional versatility of the FHA domain in DNA-damage signaling by the tumor suppressor kinase Chk2", Mol Cell. 2002;9:1045-54.

Li H. et al., "Structure of human Ki67 FHA domain and its binding to a phosphoprotein fragment from hNIFK reveal unique recognition sites and new views to the structural basis of FHA domain functions", J Mol Biol. 2004;335:371-81.

Liao H. et al., "Structure of the FHA1 domain of yeast Rad53 and identification of binding sites for both FHA1 and its target protein Rad9", J Mol Biol. 2000;304:941-51.

Lu PJ et al., "Function of WW domains as phosphoserine- or phosphothreonine-binding modules", Science. 1999;283:1325-8.

Mahajan A. et al., "FHA domain-ligand interactions: importance of integrating chemical and biological approaches", J Am Chem Soc. 2005;127:14572-3.

Mahajan A. et al., "Structure and function of the phosphothreonine-specific FHA domain", Sci Signal. 2008;1:re12.

Manning G. et al., "The protein kinase complement of the human genome", Science. 2002;298:1912-34.

Mohammad DH et al., "14-3-3 proteins, FHA domains and BRCT domains in the DNA damage response" DNA Repair (Amst) 2009;8:1009-17.

Muslin AJ et al., "Interaction of 14—3—3 with signaling proteins is mediated by the recognition of phosphoserine", Cell. 1996;84:889-97.

Paschke M. et al., "A twin-arginine translocation (Tat)-mediated phage display system", Gene. 2005;350:79-88.

Pawson T. et al., "Assembly of cell regulatory systems through protein interaction domains", Science. 2003;300:445-52.

Pennell S. et al., "Structural and functional analysis of phosphothreonine-dependent FHA domain interactions", Structure. 2010;18:1587-95.

Pershad K. et al., "Drop-out phagemid vector for switching from phage displayed affinity reagents to expression formats", Anal Biochem. 2011;412:210-6.

Schaefer JV et al., "Improving Expression of scFv Fragments by Co-expression of Periplasmic Chaperones", In: Kontermann R, Dübel S, editors. Antibody engineering. 2. Springer-Verlag; Berlin Heidelberg: 2010. pp. 345-361.

Schlessinger J. et al., "SH2 and PTB domains in tyrosine kinase signaling", Sci STKE. 2003;2003:RE12.

Sefton BM, Shenolikar S. Overview of protein phosphorylation. Curr Protoc Protein Sci. 2001;Ch. 13, Unit13-1.

Sidhu SS. et al., "Phage display for selection of novel binding peptides", Methods Enzymol. 2000;328:333-63.

Skowyra D. et al., "F-box proteins are receptors that recruit phosphorylated substrates to the SCF ubiquitin-ligase complex", Cell. 1997;91:209-19.

Sun T. et al., "Preparation and application of antibodies to phosphoamino acid sequences", Biopolymers. 2001;60:61-75.

Tsai MD, "FHA: a signal transduction domain with diverse specificity and function", Structure. 2002;10:887-8.

Wang P. et al., "Yongkiettrakul S, Pei D, Tsai MD. II. Structure and specificity of the interaction between the FHA2 domain of Rad53 and phosphotyrosyl peptides", J Mol Biol. 2000;302:927-40.

Williams RS et al., "Structural basis of phosphopeptide recognition by the BRCT domain of BRCA1", Nat Struct Mol Biol. 2004;11:519-25.

Wu LF et al., "Bacterial twin-arginine signal peptide-dependent protein translocation pathway: evolution and mechanism", J Mol Microbiol Biotechnol. 2000;2:179-89.

Yaffe MB et al., "Phosphoserine/threonine-binding domains", Curr Opin Cell Biol. 2001;13:131-8.

Yaffe MB, "Phosphotyrosine-binding domains in signal transduction", Nat Rev Mol Cell Biol. 2002;3:177-86.

Yongkiettrakul S. et al., "The ligand specificity of yeast Rad53 FHA domains at the +3 position is determined by nonconserved residues", Biochemistry. 2004;43:3862-9.

Figure 9
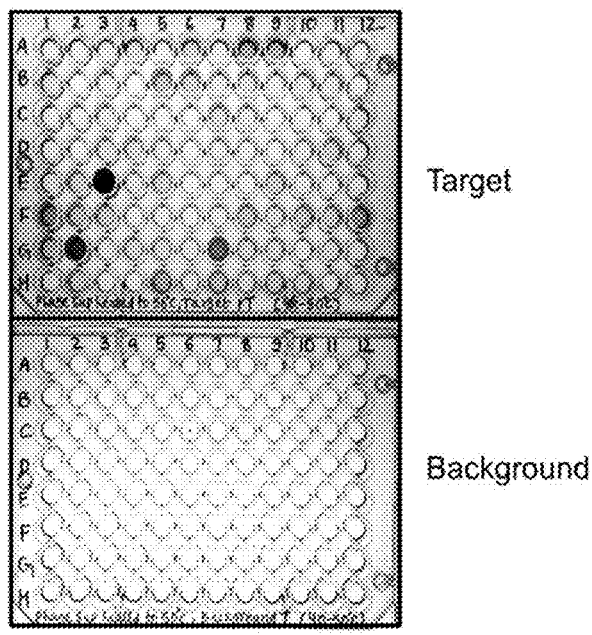
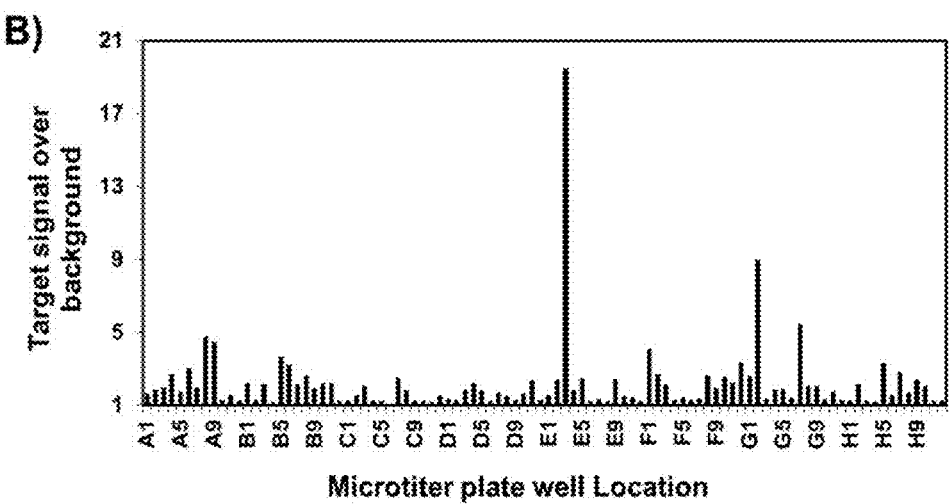

SEQUENCE LISTING

```
<160> NUMBER OF SEQ ID NOS: 97

<210> SEQ ID NO 1
<211> LENGTH: 18
<212> TYPE: PRT
<213> ORGANISM: artificial sequence
<220> FEATURE:
<223> OTHER INFORMATION: phosphopeptide SGS-Rad9-pT
<220> FEATURE:
<221> NAME/KEY: MOD_RES
<222> LOCATION: (8)..(8)
<223> OTHER INFORMATION: PHOSPHORYLATION

<400> SEQUENCE: 1

Ser Gly Ser Ser Leu Glu Val Thr Glu Ala Asp Ala Thr Phe Tyr Ala
```

-continued

```
1               5                   10                  15
Lys Lys

<210> SEQ ID NO 2
<211> LENGTH: 18
<212> TYPE: PRT
<213> ORGANISM: artificial sequence
<220> FEATURE:
<223> OTHER INFORMATION: peptide SGS-Rad9-T

<400> SEQUENCE: 2

Ser Gly Ser Ser Leu Glu Val Thr Glu Ala Asp Ala Thr Phe Tyr Ala
1               5                   10                  15

Lys Lys

<210> SEQ ID NO 3
<211> LENGTH: 18
<212> TYPE: PRT
<213> ORGANISM: artificial sequence
<220> FEATURE:
<223> OTHER INFORMATION: phosphopeptide SGS-Rad9-pS
<220> FEATURE:
<221> NAME/KEY: MOD_RES
<222> LOCATION: (8)..(8)
<223> OTHER INFORMATION: PHOSPHORYLATION

<400> SEQUENCE: 3

Ser Gly Ser Ser Leu Glu Val Ser Glu Ala Asp Ala Thr Phe Tyr Ala
1               5                   10                  15

Lys Lys

<210> SEQ ID NO 4
<211> LENGTH: 18
<212> TYPE: PRT
<213> ORGANISM: artificial sequence
<220> FEATURE:
<223> OTHER INFORMATION: phosphopeptide SGS-Rad9-pY
<220> FEATURE:
<221> NAME/KEY: MOD_RES
<222> LOCATION: (8)..(8)
<223> OTHER INFORMATION: PHOSPHORYLATION

<400> SEQUENCE: 4

Ser Gly Ser Ser Leu Glu Val Tyr Glu Ala Asp Ala Thr Phe Tyr Ala
1               5                   10                  15

Lys Lys

<210> SEQ ID NO 5
<211> LENGTH: 17
<212> TYPE: PRT
<213> ORGANISM: artificial sequence
<220> FEATURE:
<223> OTHER INFORMATION: phosphopeptide SGS-Plk1-pT
<220> FEATURE:
<221> NAME/KEY: MOD_RES
<222> LOCATION: (10)..(10)
<223> OTHER INFORMATION: PHOSPHORYLATION

<400> SEQUENCE: 5

Ser Gly Ser Ala Gly Pro Met Gln Ser Thr Pro Leu Asn Gly Ala Lys
1               5                   10                  15

Lys

<210> SEQ ID NO 6
<211> LENGTH: 17
```

```
<212> TYPE: PRT
<213> ORGANISM: artificial sequence
<220> FEATURE:
<223> OTHER INFORMATION: phosphopeptide SGS-BRCT-pS
<220> FEATURE:
<221> NAME/KEY: MOD_RES
<222> LOCATION: (8)..(8)
<223> OTHER INFORMATION: PHOSPHORYLATION

<400> SEQUENCE: 6

Ser Gly Ser Ala Tyr Asp Ile Ser Gln Val Phe Pro Phe Ala Lys Lys
1               5                   10                  15

Lys

<210> SEQ ID NO 7
<211> LENGTH: 170
<212> TYPE: PRT
<213> ORGANISM: Saccharomyces cerevisiae

<400> SEQUENCE: 7

Met Glu Asn Ile Thr Gln Pro Thr Gln Gln Ser Thr Gln Ala Thr Gln
1               5                   10                  15

Arg Phe Leu Ile Glu Lys Phe Ser Gln Glu Gln Ile Gly Glu Asn Ile
            20                  25                  30

Val Cys Arg Val Ile Cys Thr Thr Gly Gln Ile Pro Ile Arg Asp Leu
        35                  40                  45

Ser Ala Asp Ile Ser Gln Val Leu Lys Glu Lys Arg Ser Ile Lys Lys
    50                  55                  60

Val Trp Thr Phe Gly Arg Asn Pro Ala Cys Asp Tyr His Leu Gly Asn
65                  70                  75                  80

Ile Ser Arg Leu Ser Asn Lys His Phe Gln Ile Leu Leu Gly Glu Asp
                85                  90                  95

Gly Asn Leu Leu Leu Asn Asp Ile Ser Thr Asn Gly Thr Trp Leu Asn
            100                 105                 110

Gly Gln Lys Val Glu Lys Asn Ser Asn Gln Leu Leu Ser Gln Gly Asp
        115                 120                 125

Glu Ile Thr Val Gly Val Gly Val Glu Ser Asp Ile Leu Ser Leu Val
    130                 135                 140

Ile Phe Ile Asn Asp Lys Phe Lys Gln Cys Leu Glu Gln Asn Lys Val
145                 150                 155                 160

Asp Arg Ile Arg Ser Asn Leu Lys Asn Thr
                165                 170

<210> SEQ ID NO 8
<211> LENGTH: 821
<212> TYPE: PRT
<213> ORGANISM: Saccharomyces cerevisiae

<400> SEQUENCE: 8

Met Glu Asn Ile Thr Gln Pro Thr Gln Gln Ser Thr Gln Ala Thr Gln
1               5                   10                  15

Arg Phe Leu Ile Glu Lys Phe Ser Gln Glu Gln Ile Gly Glu Asn Ile
            20                  25                  30

Val Cys Arg Val Ile Cys Thr Thr Gly Gln Ile Pro Ile Arg Asp Leu
        35                  40                  45

Ser Ala Asp Ile Ser Gln Val Leu Lys Glu Lys Arg Ser Ile Lys Lys
    50                  55                  60

Val Trp Thr Phe Gly Arg Asn Pro Ala Cys Asp Tyr His Leu Gly Asn
65                  70                  75                  80
```

```
Ile Ser Arg Leu Ser Asn Lys His Phe Gln Ile Leu Gly Glu Asp
                85                  90                  95

Gly Asn Leu Leu Leu Asn Asp Ile Ser Thr Asn Gly Thr Trp Leu Asn
                100                 105                 110

Gly Gln Lys Val Glu Lys Asn Ser Asn Gln Leu Leu Ser Gln Gly Asp
                115                 120                 125

Glu Ile Thr Val Gly Val Gly Val Glu Ser Asp Ile Leu Ser Leu Val
    130                 135                 140

Ile Phe Ile Asn Asp Lys Phe Lys Gln Cys Leu Glu Gln Asn Lys Val
145                 150                 155                 160

Asp Arg Ile Arg Ser Asn Leu Lys Asn Thr Ser Lys Ile Ala Ser Pro
                165                 170                 175

Gly Leu Thr Ser Ser Thr Ala Ser Ser Met Val Ala Asn Lys Thr Gly
                180                 185                 190

Ile Phe Lys Asp Phe Ser Ile Ile Asp Glu Val Val Gly Gln Gly Ala
                195                 200                 205

Phe Ala Thr Val Lys Lys Ala Ile Glu Arg Thr Thr Gly Lys Thr Phe
    210                 215                 220

Ala Val Lys Ile Ile Ser Lys Arg Lys Val Ile Gly Asn Met Asp Gly
225                 230                 235                 240

Val Thr Arg Glu Leu Glu Val Leu Gln Lys Leu Asn His Pro Arg Ile
                245                 250                 255

Val Arg Leu Lys Gly Phe Tyr Glu Asp Thr Glu Ser Tyr Tyr Met Val
                260                 265                 270

Met Glu Phe Val Ser Gly Gly Asp Leu Met Asp Phe Val Ala Ala His
                275                 280                 285

Gly Ala Val Gly Glu Asp Ala Gly Arg Glu Ile Ser Arg Gln Ile Leu
    290                 295                 300

Thr Ala Ile Lys Tyr Ile His Ser Met Gly Ile Ser His Arg Asp Leu
305                 310                 315                 320

Lys Pro Asp Asn Ile Leu Ile Glu Gln Asp Asp Pro Val Leu Val Lys
                325                 330                 335

Ile Thr Asp Phe Gly Leu Ala Lys Val Gln Gly Asn Gly Ser Phe Met
                340                 345                 350

Lys Thr Phe Cys Gly Thr Leu Ala Tyr Val Ala Pro Glu Val Ile Arg
                355                 360                 365

Gly Lys Asp Thr Ser Val Ser Pro Asp Glu Tyr Glu Glu Arg Asn Glu
    370                 375                 380

Tyr Ser Ser Leu Val Asp Met Trp Ser Met Gly Cys Leu Val Tyr Val
385                 390                 395                 400

Ile Leu Thr Gly His Leu Pro Phe Ser Gly Ser Thr Gln Asp Gln Leu
                405                 410                 415

Tyr Lys Gln Ile Gly Arg Gly Ser Tyr His Glu Gly Pro Leu Lys Asp
                420                 425                 430

Phe Arg Ile Ser Glu Glu Ala Arg Asp Phe Ile Asp Ser Leu Leu Gln
                435                 440                 445

Val Asp Pro Asn Asn Arg Ser Thr Ala Ala Lys Ala Leu Asn His Pro
    450                 455                 460

Trp Ile Lys Met Ser Pro Leu Gly Ser Gln Ser Tyr Gly Asp Phe Ser
465                 470                 475                 480

Gln Ile Ser Leu Ser Gln Ser Leu Ser Gln Gln Lys Leu Leu Glu Asn
                485                 490                 495
```

```
Met Asp Asp Ala Gln Tyr Glu Phe Val Lys Ala Gln Arg Lys Leu Gln
                500                 505                 510

Met Glu Gln Gln Leu Gln Glu Gln Asp Gln Glu Asp Gln Asp Gly Lys
            515                 520                 525

Ile Gln Gly Phe Lys Ile Pro Ala His Ala Pro Ile Arg Tyr Thr Gln
        530                 535                 540

Pro Lys Ser Ile Glu Ala Glu Thr Arg Glu Gln Lys Leu Leu His Ser
545                 550                 555                 560

Asn Asn Thr Glu Asn Val Lys Ser Ser Lys Lys Gly Asn Gly Arg
                565                 570                 575

Phe Leu Thr Leu Lys Pro Leu Pro Asp Ser Ile Ile Gln Glu Ser Leu
                580                 585                 590

Glu Ile Gln Gln Gly Val Asn Pro Phe Phe Ile Gly Arg Ser Glu Asp
                595                 600                 605

Cys Asn Cys Lys Ile Glu Asp Asn Arg Leu Ser Arg Val His Cys Phe
            610                 615                 620

Ile Phe Lys Lys Arg His Ala Val Gly Lys Ser Met Tyr Glu Ser Pro
625                 630                 635                 640

Ala Gln Gly Leu Asp Asp Ile Trp Tyr Cys His Thr Gly Thr Asn Val
                645                 650                 655

Ser Tyr Leu Asn Asn Asn Arg Met Ile Gln Gly Thr Lys Phe Leu Leu
                660                 665                 670

Gln Asp Gly Asp Glu Ile Lys Ile Ile Trp Asp Lys Asn Asn Lys Phe
            675                 680                 685

Val Ile Gly Phe Lys Val Glu Ile Asn Asp Thr Thr Gly Leu Phe Asn
            690                 695                 700

Glu Gly Leu Gly Met Leu Gln Glu Gln Arg Val Val Leu Lys Gln Thr
705                 710                 715                 720

Ala Glu Glu Lys Asp Leu Val Lys Lys Leu Thr Gln Met Met Ala Ala
                725                 730                 735

Gln Arg Ala Asn Gln Pro Ser Ala Ser Ser Ser Met Ser Ala Lys
            740                 745                 750

Lys Pro Pro Val Ser Asp Thr Asn Asn Asn Gly Asn Asn Ser Val Leu
            755                 760                 765

Asn Asp Leu Val Glu Ser Pro Ile Asn Ala Asn Thr Gly Asn Ile Leu
            770                 775                 780

Lys Arg Ile His Ser Val Ser Leu Ser Gln Ser Gln Ile Asp Pro Ser
785                 790                 795                 800

Lys Lys Val Lys Arg Ala Lys Leu Asp Gln Thr Ser Lys Gly Pro Glu
                805                 810                 815

Asn Leu Gln Phe Ser
            820

<210> SEQ ID NO 9
<211> LENGTH: 15
<212> TYPE: PRT
<213> ORGANISM: artificial sequence
<220> FEATURE:
<223> OTHER INFORMATION: phosphopeptide Rad9-pT
<220> FEATURE:
<221> NAME/KEY: MOD_RES
<222> LOCATION: (5)..(5)
<223> OTHER INFORMATION: PHOSPHORYLATION

<400> SEQUENCE: 9

Ser Leu Glu Val Thr Glu Ala Asp Ala Thr Phe Tyr Ala Lys Lys
1               5                   10                  15
```

<210> SEQ ID NO 10
<211> LENGTH: 33
<212> TYPE: DNA
<213> ORGANISM: artificial sequence
<220> FEATURE:
<223> OTHER INFORMATION: primer FHA1-BamH1-Fw

<400> SEQUENCE: 10
atcatcggat ccatggaaaa tattacacaa cca                                33

<210> SEQ ID NO 11
<211> LENGTH: 39
<212> TYPE: DNA
<213> ORGANISM: artificial sequence
<220> FEATURE:
<223> OTHER INFORMATION: primer FHA1-EcoR1-Rv

<400> SEQUENCE: 11
gtagatgaat tcggtatttt taagatttga acggatacg                          39

<210> SEQ ID NO 12
<211> LENGTH: 24
<212> TYPE: DNA
<213> ORGANISM: artificial sequence
<220> FEATURE:
<223> OTHER INFORMATION: primer Seq-pGEX-Fw

<400> SEQUENCE: 12
catggccttt gcagggctgg caag                                          24

<210> SEQ ID NO 13
<211> LENGTH: 35
<212> TYPE: DNA
<213> ORGANISM: artificial sequence
<220> FEATURE:
<223> OTHER INFORMATION: primer FHA1-NcoI-Fw

<400> SEQUENCE: 13
tccagcccat ggcgatggaa aatattacac aacca                              35

<210> SEQ ID NO 14
<211> LENGTH: 23
<212> TYPE: DNA
<213> ORGANISM: artificial sequence
<220> FEATURE:
<223> OTHER INFORMATION: primer FHA1-NotI-Rv

<400> SEQUENCE: 14
cgagtctaga tgcggccgcg gta                                           23

<210> SEQ ID NO 15
<211> LENGTH: 24
<212> TYPE: DNA
<213> ORGANISM: artificial sequence
<220> FEATURE:
<223> OTHER INFORMATION: primer DsbA-Fw

<400> SEQUENCE: 15
cgctggctgg tttagtttta gcgt                                          24

<210> SEQ ID NO 16
<211> LENGTH: 26
<212> TYPE: DNA
<213> ORGANISM: artificial sequence
<220> FEATURE:

<223> OTHER INFORMATION: primer MP-FHA1-Fw

<400> SEQUENCE: 16
tgctagcgcc atggcgatgg aaaata					26

<210> SEQ ID NO 17
<211> LENGTH: 24
<212> TYPE: DNA
<213> ORGANISM: artificial sequence
<220> FEATURE:
<223> OTHER INFORMATION: primer MP-FHA1-Rv

<400> SEQUENCE: 17
tcgactgcgg ccgcggtatt ttta					24

<210> SEQ ID NO 18
<211> LENGTH: 32
<212> TYPE: DNA
<213> ORGANISM: artificial sequence
<220> FEATURE:
<223> OTHER INFORMATION: primer FHA1-NdeI-Fw

<400> SEQUENCE: 18
tagctacata tgaccatggc gatggaaaat at				32

<210> SEQ ID NO 19
<211> LENGTH: 34
<212> TYPE: DNA
<213> ORGANISM: artificial sequence
<220> FEATURE:
<223> OTHER INFORMATION: primer FHA1-XhoI-Rv

<400> SEQUENCE: 19
gagctactcg aggagtgcgg ccgcggtatt ttta				34

<210> SEQ ID NO 20
<211> LENGTH: 21
<212> TYPE: DNA
<213> ORGANISM: artificial sequence
<220> FEATURE:
<223> OTHER INFORMATION: primer pET29b-Fw

<400> SEQUENCE: 20
cagcagccaa ctcagcttcc t						21

<210> SEQ ID NO 21
<211> LENGTH: 45
<212> TYPE: DNA
<213> ORGANISM: artificial sequence
<220> FEATURE:
<223> OTHER INFORMATION: primer KM-S34C+S38C-FHA

<400> SEQUENCE: 21
gaatttgacc agttgtgcag attacgcggc atacgatgtt ttcgc		45

<210> SEQ ID NO 22
<211> LENGTH: 37
<212> TYPE: DNA
<213> ORGANISM: artificial sequence
<220> FEATURE:
<223> OTHER INFORMATION: primer KM-S154C-FHA

<400> SEQUENCE: 22
gactttattt tgttccaggc attgtttgaa tttatcg			37

-continued

```
<210> SEQ ID NO 23
<211> LENGTH: 34
<212> TYPE: DNA
<213> ORGANISM: artificial sequence
<220> FEATURE:
<223> OTHER INFORMATION: primer KM-C74S-FHA1

<400> SEQUENCE: 23
acctaagtga taatcagagg ctgggttacg tcca                                34

<210> SEQ ID NO 24
<211> LENGTH: 32
<212> TYPE: DNA
<213> ORGANISM: artificial sequence
<220> FEATURE:
<223> OTHER INFORMATION: primer F-TAA

<400> SEQUENCE: 24
tgttgagatt acgcgttata cgatgttttc gc                                  32

<210> SEQ ID NO 25
<211> LENGTH: 32
<212> TYPE: DNA
<213> ORGANISM: artificial sequence
<220> FEATURE:
<223> OTHER INFORMATION: primer F-Leu

<400> SEQUENCE: 25
tgttgagatt acgcgcagta cgatgttttc gc                                  32

<210> SEQ ID NO 26
<211> LENGTH: 32
<212> TYPE: DNA
<213> ORGANISM: artificial sequence
<220> FEATURE:
<223> OTHER INFORMATION: primer F-Ile

<400> SEQUENCE: 26
tgttgagatt acgcgaatta cgatgttttc gc                                  32

<210> SEQ ID NO 27
<211> LENGTH: 32
<212> TYPE: DNA
<213> ORGANISM: artificial sequence
<220> FEATURE:
<223> OTHER INFORMATION: primer F-Met

<400> SEQUENCE: 27
tgttgagatt acgcgcatta cgatgttttc gc                                  32

<210> SEQ ID NO 28
<211> LENGTH: 32
<212> TYPE: DNA
<213> ORGANISM: artificial sequence
<220> FEATURE:
<223> OTHER INFORMATION: primer F-Val

<400> SEQUENCE: 28
tgttgagatt acgcgaacta cgatgttttc gc                                  32

<210> SEQ ID NO 29
<211> LENGTH: 32
<212> TYPE: DNA
<213> ORGANISM: artificial sequence
<220> FEATURE:
<223> OTHER INFORMATION: primer F-Pro
```

<400> SEQUENCE: 29
tgttgagatt acgcgcggta cgatgttttc gc                                    32

<210> SEQ ID NO 30
<211> LENGTH: 32
<212> TYPE: DNA
<213> ORGANISM: artificial sequence
<220> FEATURE:
<223> OTHER INFORMATION: primer F-Thr

<400> SEQUENCE: 30
tgttgagatt acgcgggtta cgatgttttc gc                                    32

<210> SEQ ID NO 31
<211> LENGTH: 32
<212> TYPE: DNA
<213> ORGANISM: artificial sequence
<220> FEATURE:
<223> OTHER INFORMATION: primer F-Ala

<400> SEQUENCE: 31
tgttgagatt acgcgtgcta cgatgttttc gc                                    32

<210> SEQ ID NO 32
<211> LENGTH: 32
<212> TYPE: DNA
<213> ORGANISM: artificial sequence
<220> FEATURE:
<223> OTHER INFORMATION: primer F-Tyr

<400> SEQUENCE: 32
tgttgagatt acgcgatata cgatgttttc gc                                    32

<210> SEQ ID NO 33
<211> LENGTH: 32
<212> TYPE: DNA
<213> ORGANISM: artificial sequence
<220> FEATURE:
<223> OTHER INFORMATION: primer F-His

<400> SEQUENCE: 33
tgttgagatt acgcggtgta cgatgttttc gc                                    32

<210> SEQ ID NO 34
<211> LENGTH: 32
<212> TYPE: DNA
<213> ORGANISM: artificial sequence
<220> FEATURE:
<223> OTHER INFORMATION: primer F-Asn

<400> SEQUENCE: 34
tgttgagatt acgcggttta cgatgttttc gc                                    32

<210> SEQ ID NO 35
<211> LENGTH: 32
<212> TYPE: DNA
<213> ORGANISM: artificial sequence
<220> FEATURE:
<223> OTHER INFORMATION: primer F-Lys

<400> SEQUENCE: 35
tgttgagatt acgcgtttta cgatgttttc gc                                    32

<210> SEQ ID NO 36
<211> LENGTH: 32

<210> SEQ ID NO 36
<211> LENGTH: 32
<212> TYPE: DNA
<213> ORGANISM: artificial sequence
<220> FEATURE:
<223> OTHER INFORMATION: primer F-Asp

<400> SEQUENCE: 36
tgttgagatt acgcgatcta cgatgttttc gc         32

<210> SEQ ID NO 37
<211> LENGTH: 32
<212> TYPE: DNA
<213> ORGANISM: artificial sequence
<220> FEATURE:
<223> OTHER INFORMATION: primer F-Glu

<400> SEQUENCE: 37
tgttgagatt acgcgttcta cgatgttttc gc         32

<210> SEQ ID NO 38
<211> LENGTH: 32
<212> TYPE: DNA
<213> ORGANISM: artificial sequence
<220> FEATURE:
<223> OTHER INFORMATION: primer F-Cys

<400> SEQUENCE: 38
tgttgagatt acgcgacata cgatgttttc gc         32

<210> SEQ ID NO 39
<211> LENGTH: 32
<212> TYPE: DNA
<213> ORGANISM: artificial sequence
<220> FEATURE:
<223> OTHER INFORMATION: primer F-Trp

<400> SEQUENCE: 39
tgttgagatt acgcgccata cgatgttttc gc         32

<210> SEQ ID NO 40
<211> LENGTH: 32
<212> TYPE: DNA
<213> ORGANISM: artificial sequence
<220> FEATURE:
<223> OTHER INFORMATION: primer F-Arg

<400> SEQUENCE: 40
tgttgagatt acgcgacgta cgatgttttc gc         32

<210> SEQ ID NO 41
<211> LENGTH: 32
<212> TYPE: DNA
<213> ORGANISM: artificial sequence
<220> FEATURE:
<223> OTHER INFORMATION: primer F-Gly

<400> SEQUENCE: 41
tgttgagatt acgcggccta cgatgttttc gc         32

<210> SEQ ID NO 42
<211> LENGTH: 32
<212> TYPE: DNA
<213> ORGANISM: artificial sequence
<220> FEATURE:
<223> OTHER INFORMATION: primer F-Glu

<400> SEQUENCE: 42

-continued tgttgagatt acgcgctgta cgatgttttc gc                          32

<210> SEQ ID NO 43
<211> LENGTH: 33
<212> TYPE: DNA
<213> ORGANISM: artificial sequence
<220> FEATURE:
<223> OTHER INFORMATION: primer KM-G2-L78A

<400> SEQUENCE: 43
gcggctaatg ttacccgcgt gataatcgca ggc                         33

<210> SEQ ID NO 44
<211> LENGTH: 29
<212> TYPE: DNA
<213> ORGANISM: artificial sequence
<220> FEATURE:
<223> OTHER INFORMATION: primer KM-G2-G79A

<400> SEQUENCE: 44
gcggctaatg ttcgctaagt gataatcgc                              29

<210> SEQ ID NO 45
<211> LENGTH: 33
<212> TYPE: DNA
<213> ORGANISM: artificial sequence
<220> FEATURE:
<223> OTHER INFORMATION: primer KM-G2-N80A

<400> SEQUENCE: 45
agataagcgg ctaatcgcac ctaagtgata atc                         33

<210> SEQ ID NO 46
<211> LENGTH: 33
<212> TYPE: DNA
<213> ORGANISM: artificial sequence
<220> FEATURE:
<223> OTHER INFORMATION: primer KM-G2-I81A

<400> SEQUENCE: 46
attagataag cggctcgcgt tacctaagtg ata                         33

<210> SEQ ID NO 47
<211> LENGTH: 38
<212> TYPE: DNA
<213> ORGANISM: artificial sequence
<220> FEATURE:
<223> OTHER INFORMATION: primer KM-G2-S82A

<400> SEQUENCE: 47
gtgtttatta gataagcgcg caatgttacc taagtgat                    38

<210> SEQ ID NO 48
<211> LENGTH: 41
<212> TYPE: DNA
<213> ORGANISM: artificial sequence
<220> FEATURE:
<223> OTHER INFORMATION: primer KM-G2-R83A

<400> SEQUENCE: 48
gaaagtgttt attagataac gcgctaatgt tacctaagtg a                41

<210> SEQ ID NO 49
<211> LENGTH: 31
<212> TYPE: DNA
<213> ORGANISM: artificial sequence
<220> FEATURE:
<223> OTHER INFORMATION: primer KM-G2-L84A

<400> SEQUENCE: 49
gtgtttatta gacgcgcggc taatgttacc t                     31

<210> SEQ ID NO 50
<211> LENGTH: 38
<212> TYPE: DNA
<213> ORGANISM: artificial sequence
<220> FEATURE:
<223> OTHER INFORMATION: primer KM-G2-S85A

<400> SEQUENCE: 50
gatttgaaag tgtttattcg ctaagcggct aatgttac               38

<210> SEQ ID NO 51
<211> LENGTH: 38
<212> TYPE: DNA
<213> ORGANISM: artificial sequence
<220> FEATURE:
<223> OTHER INFORMATION: primer KM-G2-N86A

<400> SEQUENCE: 51
gaggatttga aagtgtttcg cagataagcg gctaatgt               38

<210> SEQ ID NO 52
<211> LENGTH: 39
<212> TYPE: DNA
<213> ORGANISM: artificial sequence
<220> FEATURE:
<223> OTHER INFORMATION: primer KM-G2-K87A

<400> SEQUENCE: 52
caggaggatt tgaaagtgcg cattagataa gcggctaat              39

<210> SEQ ID NO 53
<211> LENGTH: 39
<212> TYPE: DNA
<213> ORGANISM: artificial sequence
<220> FEATURE:
<223> OTHER INFORMATION: primer KM-G2-H88A

<400> SEQUENCE: 53
gcccaggagg atttgaaacg ctttattaga taagcggct              39

<210> SEQ ID NO 54
<211> LENGTH: 38
<212> TYPE: DNA
<213> ORGANISM: artificial sequence
<220> FEATURE:
<223> OTHER INFORMATION: primer KM-G2-G133A

<400> SEQUENCE: 54
atcgctttct acacctaccg ctaccgtaat ttcgtcgc               38

<210> SEQ ID NO 55
<211> LENGTH: 38
<212> TYPE: DNA
<213> ORGANISM: artificial sequence
<220> FEATURE:
<223> OTHER INFORMATION: primer KM-G2-V134A

<400> SEQUENCE: 55
atatcgcttt ctacacccgc gcctaccgta atttcgtc               38

```
<210> SEQ ID NO 56
<211> LENGTH: 29
<212> TYPE: DNA
<213> ORGANISM: artificial sequence
<220> FEATURE:
<223> OTHER INFORMATION: primer KM-G2-G135A

<400> SEQUENCE: 56
tatcgctttc taccgctacg cctaccgta                                29

<210> SEQ ID NO 57
<211> LENGTH: 28
<212> TYPE: DNA
<213> ORGANISM: artificial sequence
<220> FEATURE:
<223> OTHER INFORMATION: primer KM-G2-V136A

<400> SEQUENCE: 57
atatcgcttt ccgcacctac gcctaccg                                 28

<210> SEQ ID NO 58
<211> LENGTH: 33
<212> TYPE: DNA
<213> ORGANISM: artificial sequence
<220> FEATURE:
<223> OTHER INFORMATION: primer KM-G2-E137A

<400> SEQUENCE: 58
gcttaaaata tcgctcgcta cacctacgcc tac                           33

<210> SEQ ID NO 59
<211> LENGTH: 30
<212> TYPE: DNA
<213> ORGANISM: artificial sequence
<220> FEATURE:
<223> OTHER INFORMATION: primer KM-G2-S138A

<400> SEQUENCE: 59
gcttaaaata tccgcttcta cacctacgcc                               30

<210> SEQ ID NO 60
<211> LENGTH: 33
<212> TYPE: DNA
<213> ORGANISM: artificial sequence
<220> FEATURE:
<223> OTHER INFORMATION: primer KM-G2-D139A

<400> SEQUENCE: 60
gactaagctt aaaatcgcgc tttctacacc tac                           33

<210> SEQ ID NO 61
<211> LENGTH: 34
<212> TYPE: DNA
<213> ORGANISM: artificial sequence
<220> FEATURE:
<223> OTHER INFORMATION: primer KM-G2-I140A

<400> SEQUENCE: 61
atgactaagc ttaacgcatc gctttctaca ccta                          34

<210> SEQ ID NO 62
<211> LENGTH: 39
<212> TYPE: DNA
<213> ORGANISM: artificial sequence
<220> FEATURE:
<223> OTHER INFORMATION: primer KM-G2-I104A
```

<400> SEQUENCE: 62
gccatgtacc atttgttgac gcgtcgttga gtaataagt          39

<210> SEQ ID NO 63
<211> LENGTH: 38
<212> TYPE: DNA
<213> ORGANISM: artificial sequence
<220> FEATURE:
<223> OTHER INFORMATION: primer KM-G2-S105A

<400> SEQUENCE: 63
gagccatgta ccatttgtcg cgatgtcgtt gagtaata          38

<210> SEQ ID NO 64
<211> LENGTH: 36
<212> TYPE: DNA
<213> ORGANISM: artificial sequence
<220> FEATURE:
<223> OTHER INFORMATION: primer KM-G2-T106A

<400> SEQUENCE: 64
tgagccatgt accattcgct gagatgtcgt tgagta          36

<210> SEQ ID NO 65
<211> LENGTH: 37
<212> TYPE: DNA
<213> ORGANISM: artificial sequence
<220> FEATURE:
<223> OTHER INFORMATION: primer KM-G2-N107A

<400> SEQUENCE: 65
cgttgagcca tgtacccgct gttgagatgt cgttgag          37

<210> SEQ ID NO 66
<211> LENGTH: 37
<212> TYPE: DNA
<213> ORGANISM: artificial sequence
<220> FEATURE:
<223> OTHER INFORMATION: primer KM-G2-G108A

<400> SEQUENCE: 66
tgaccgttga gccatgtcgc atttgttgag atgtcgt          37

<210> SEQ ID NO 67
<211> LENGTH: 65
<212> TYPE: DNA
<213> ORGANISM: artificial sequence
<220> FEATURE:
<223> OTHER INFORMATION: primer B4-B5 Lib
<220> FEATURE:
<221> NAME/KEY: misc_feature
<222> LOCATION: (30)..(30)
<223> OTHER INFORMATION: "k" = g or t
<220> FEATURE:
<221> NAME/KEY: misc_feature
<222> LOCATION: (31)..(32)
<223> OTHER INFORMATION: "n" = a, g, c, or t
<220> FEATURE:
<221> NAME/KEY: misc_feature
<222> LOCATION: (33)..(33)
<223> OTHER INFORMATION: "k" = g or t
<220> FEATURE:
<221> NAME/KEY: misc_feature
<222> LOCATION: (34)..(35)
<223> OTHER INFORMATION: "n" = a, g, c, or t
<220> FEATURE:
<221> NAME/KEY: misc_feature
<222> LOCATION: (36)..(36)

<223> OTHER INFORMATION: "k" = g or t
<220> FEATURE:
<221> NAME/KEY: misc_feature
<222> LOCATION: (37)..(38)
<223> OTHER INFORMATION: "n" = a, g, c, or t

<400> SEQUENCE: 67

```
cccaggagga tttgaaagtg tttattagak nnknnknnaa tgttacctaa gtgataatcg    60
caggc                                                                65
```

<210> SEQ ID NO 68
<211> LENGTH: 83
<212> TYPE: DNA
<213> ORGANISM: artificial sequence
<220> FEATURE:
<223> OTHER INFORMATION: primer B10-B11 Lib
<220> FEATURE:
<221> NAME/KEY: misc_feature
<222> LOCATION: (41)..(41)
<223> OTHER INFORMATION: "k" = g or t
<220> FEATURE:
<221> NAME/KEY: misc_feature
<222> LOCATION: (42)..(43)
<223> OTHER INFORMATION: "n" = a, g, c, or t
<220> FEATURE:
<221> NAME/KEY: misc_feature
<222> LOCATION: (44)..(44)
<223> OTHER INFORMATION: "k" = g or t
<220> FEATURE:
<221> NAME/KEY: misc_feature
<222> LOCATION: (45)..(46)
<223> OTHER INFORMATION: "n" = a, g, c, or t
<220> FEATURE:
<221> NAME/KEY: misc_feature
<222> LOCATION: (47)..(47)
<223> OTHER INFORMATION: "k" = g or t
<220> FEATURE:
<221> NAME/KEY: misc_feature
<222> LOCATION: (48)..(49)
<223> OTHER INFORMATION: "n" = a, g, c, or t
<220> FEATURE:
<221> NAME/KEY: misc_feature
<222> LOCATION: (50)..(50)
<223> OTHER INFORMATION: "k" = g or t
<220> FEATURE:
<221> NAME/KEY: misc_feature
<222> LOCATION: (51)..(52)
<223> OTHER INFORMATION: "n" = a, g, c, or t
<220> FEATURE:
<221> NAME/KEY: misc_feature
<222> LOCATION: (53)..(53)
<223> OTHER INFORMATION: "k" = g or t
<220> FEATURE:
<221> NAME/KEY: misc_feature
<222> LOCATION: (54)..(55)
<223> OTHER INFORMATION: "n" = a, g, c, or t
<220> FEATURE:
<221> NAME/KEY: misc_feature
<222> LOCATION: (56)..(56)
<223> OTHER INFORMATION: "k" = g or t
<220> FEATURE:
<221> NAME/KEY: misc_feature
<222> LOCATION: (57)..(58)
<223> OTHER INFORMATION: "n" = a, g, c, or t
<220> FEATURE:
<221> NAME/KEY: misc_feature
<222> LOCATION: (59)..(59)
<223> OTHER INFORMATION: "k" = g or t
<220> FEATURE:
<221> NAME/KEY: misc_feature
<222> LOCATION: (60)..(61)
<223> OTHER INFORMATION: "n" = a, g, c, or t

<400> SEQUENCE: 68

```
gtttgaattt atcgttaata aaaatgacta agcttaaaat knnknnknnk nnknnknnkn    60
```

```
ntaccgtaat ttcgtcgcct tga                                              83
```

<210> SEQ ID NO 69
<211> LENGTH: 62
<212> TYPE: DNA
<213> ORGANISM: artificial sequence
<220> FEATURE:
<223> OTHER INFORMATION: primer pKP700-G2-XmaI#1

<400> SEQUENCE: 69

```
ccaggaggat tgaaagtgt tattagacc cggggctaat gttacctaag tgataatcgc        60
ag                                                                     62
```

<210> SEQ ID NO 70
<211> LENGTH: 65
<212> TYPE: DNA
<213> ORGANISM: artificial sequence
<220> FEATURE:
<223> OTHER INFORMATION: primer pKP700-G2-XmaI#2

<400> SEQUENCE: 70

```
cgttaataaa aatgactaag cttaaaatat cgctttcccc gggtacgcct accgtaattt      60
cgtcg                                                                  65
```

<210> SEQ ID NO 71
<211> LENGTH: 65
<212> TYPE: DNA
<213> ORGANISM: artificial sequence
<220> FEATURE:
<223> OTHER INFORMATION: primer Phos B4-B5 Lib
<220> FEATURE:
<221> NAME/KEY: misc_feature
<222> LOCATION: (1)..(1)
<223> OTHER INFORMATION: PHOSPHORYLATION
<220> FEATURE:
<221> NAME/KEY: misc_feature
<222> LOCATION: (30)..(30)
<223> OTHER INFORMATION: "k" = g or t
<220> FEATURE:
<221> NAME/KEY: misc_feature
<222> LOCATION: (31)..(32)
<223> OTHER INFORMATION: "n" = a, g, c, or t
<220> FEATURE:
<221> NAME/KEY: misc_feature
<222> LOCATION: (33)..(33)
<223> OTHER INFORMATION: "k" = g or t
<220> FEATURE:
<221> NAME/KEY: misc_feature
<222> LOCATION: (34)..(35)
<223> OTHER INFORMATION: "n" = a, g, c, or t
<220> FEATURE:
<221> NAME/KEY: misc_feature
<222> LOCATION: (36)..(36)
<223> OTHER INFORMATION: "k" = g or t
<220> FEATURE:
<221> NAME/KEY: misc_feature
<222> LOCATION: (37)..(38)
<223> OTHER INFORMATION: "n" = a, g, c, or t

<400> SEQUENCE: 71

```
cccaggagga tttgaaagtg tttattagak nnknnknnaa tgttacctaa gtgataatcg      60
caggc                                                                  65
```

<210> SEQ ID NO 72
<211> LENGTH: 83
<212> TYPE: DNA
<213> ORGANISM: artificial sequence
<220> FEATURE:

```
<223> OTHER INFORMATION: primer Phos B10-B11 Lib
<220> FEATURE:
<221> NAME/KEY: misc_feature
<222> LOCATION: (1)..(1)
<223> OTHER INFORMATION: PHOSPHORYLATION
<220> FEATURE:
<221> NAME/KEY: misc_feature
<222> LOCATION: (41)..(41)
<223> OTHER INFORMATION: "k" = g or t
<220> FEATURE:
<221> NAME/KEY: misc_feature
<222> LOCATION: (42)..(43)
<223> OTHER INFORMATION: "n" = a, g, c, or t
<220> FEATURE:
<221> NAME/KEY: misc_feature
<222> LOCATION: (44)..(44)
<223> OTHER INFORMATION: "k" = g or t
<220> FEATURE:
<221> NAME/KEY: misc_feature
<222> LOCATION: (45)..(46)
<223> OTHER INFORMATION: "n" = a, g, c, or t
<220> FEATURE:
<221> NAME/KEY: misc_feature
<222> LOCATION: (47)..(47)
<223> OTHER INFORMATION: "k" = g or t
<220> FEATURE:
<221> NAME/KEY: misc_feature
<222> LOCATION: (48)..(49)
<223> OTHER INFORMATION: "n" = a, g, c, or t
<220> FEATURE:
<221> NAME/KEY: misc_feature
<222> LOCATION: (50)..(50)
<223> OTHER INFORMATION: "k" = g or t
<220> FEATURE:
<221> NAME/KEY: misc_feature
<222> LOCATION: (51)..(52)
<223> OTHER INFORMATION: "n" = a, g, c, or t
<220> FEATURE:
<221> NAME/KEY: misc_feature
<222> LOCATION: (53)..(53)
<223> OTHER INFORMATION: "k" = g or t
<220> FEATURE:
<221> NAME/KEY: misc_feature
<222> LOCATION: (54)..(55)
<223> OTHER INFORMATION: "n" = a, g, c, or t
<220> FEATURE:
<221> NAME/KEY: misc_feature
<222> LOCATION: (56)..(56)
<223> OTHER INFORMATION: "k" = g or t
<220> FEATURE:
<221> NAME/KEY: misc_feature
<222> LOCATION: (57)..(58)
<223> OTHER INFORMATION: "n" = a, g, c, or t
<220> FEATURE:
<221> NAME/KEY: misc_feature
<222> LOCATION: (59)..(59)
<223> OTHER INFORMATION: "k" = g or t
<220> FEATURE:
<221> NAME/KEY: misc_feature
<222> LOCATION: (60)..(61)
<223> OTHER INFORMATION: "n" = a, g, c, or t

<400> SEQUENCE: 72
gtttgaattt atcgttaata aaaatgacta agcttaaaat knnknnknnk nnknnknnkn    60
ntaccgtaat ttcgtcgcct tga                                           83

<210> SEQ ID NO 73
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 73
```

His Asp His Thr Gly Phe Leu Thr Glu Tyr Val Ala Thr Lys Lys
1               5                   10                  15

<210> SEQ ID NO 74
<211> LENGTH: 17
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 74

Ala Asp Pro Glu His Asp His Thr Gly Phe Leu Thr Glu Tyr Lys Lys
1               5                   10                  15

Lys

<210> SEQ ID NO 75
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 75

His Thr Gly Phe Leu Thr Glu Tyr Val Ala Thr Arg Trp Tyr Arg
1               5                   10                  15

<210> SEQ ID NO 76
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 76

Glu Ala Arg Ser Arg Asp Ala Thr Pro Pro Val Ser Pro Tyr Lys Lys
1               5                   10                  15

<210> SEQ ID NO 77
<211> LENGTH: 15
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION

<400> SEQUENCE: 77

Ile Val Ala Asp Gln Thr Pro Thr Pro Thr Arg Phe Leu Lys Tyr
1               5                   10                  15

<210> SEQ ID NO 78
<211> LENGTH: 17
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

```
<400> SEQUENCE: 78

Ala Leu Lys Asp Glu Pro Gln Thr Val Pro Asp Val Pro Tyr Lys Lys
1               5                   10                  15

Lys

<210> SEQ ID NO 79
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 79

Lys Lys Phe Glu Leu Leu Pro Thr Pro Pro Leu Ser Pro Ser Tyr
1               5                   10                  15

<210> SEQ ID NO 80
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 80

Gly Ser Phe Val Asn Lys Pro Thr Arg Gly Trp Leu His Lys Lys
1               5                   10                  15

<210> SEQ ID NO 81
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 81

Arg Met His Leu Pro Ser Pro Thr Asp Ser Asn Phe Tyr Arg Ala
1               5                   10                  15

<210> SEQ ID NO 82
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 82

Ser Pro Thr Asp Ser Asn Phe Tyr Arg Ala Leu Met Asp Lys Lys
1               5                   10                  15

<210> SEQ ID NO 83
<211> LENGTH: 15
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 83
```

```
Thr Phe Leu Pro Val Pro Glu Tyr Ile Asn Gln Ser Val Lys Lys
1               5                   10                  15
```

<210> SEQ ID NO 84
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 84

```
Asp Thr Glu Phe Thr Ser Arg Thr Pro Lys Asp Ser Pro Tyr Lys Lys
1               5                   10                  15
```

<210> SEQ ID NO 85
<211> LENGTH: 16
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: PHOSPHORYLATION

<400> SEQUENCE: 85

```
Leu Arg Leu Asn Gln Pro Gly Thr Pro Thr Arg Thr Ala Tyr Lys Lys
1               5                   10                  15
```

<210> SEQ ID NO 86
<211> LENGTH: 9
<212> TYPE: PRT
<213> ORGANISM: artificial sequence
<220> FEATURE:
<223> OTHER INFORMATION: peptide variant of MAPK3

<400> SEQUENCE: 86

```
Ala Ala Ala Ala Thr Ala Ala Ala Ala
1               5
```

<210> SEQ ID NO 87
<211> LENGTH: 9
<212> TYPE: PRT
<213> ORGANISM: artificial sequence
<220> FEATURE:
<223> OTHER INFORMATION: peptide variant of MAPK3

<400> SEQUENCE: 87

```
Ala Ala Ala Ala Thr Ala Ala Leu Ala
1               5
```

<210> SEQ ID NO 88
<211> LENGTH: 9
<212> TYPE: PRT
<213> ORGANISM: artificial sequence
<220> FEATURE:
<223> OTHER INFORMATION: peptide variant of MAPK3

<400> SEQUENCE: 88

```
Glu His Asp His Thr Gly Phe Leu Ala
1               5
```

<210> SEQ ID NO 89
<211> LENGTH: 9
<212> TYPE: PRT
<213> ORGANISM: artificial sequence
<220> FEATURE:

-continued

<223> OTHER INFORMATION: peptide variant of MAPK3

<400> SEQUENCE: 89

Glu His Asp His Thr Gly Phe Ala Thr
1               5

<210> SEQ ID NO 90
<211> LENGTH: 9
<212> TYPE: PRT
<213> ORGANISM: artificial sequence
<220> FEATURE:
<223> OTHER INFORMATION: peptide variant of MAPK3

<400> SEQUENCE: 90

Glu His Asp His Thr Gly Ala Leu Thr
1               5

<210> SEQ ID NO 91
<211> LENGTH: 9
<212> TYPE: PRT
<213> ORGANISM: artificial sequence
<220> FEATURE:
<223> OTHER INFORMATION: peptide variant of MAPK3

<400> SEQUENCE: 91

Glu His Asp His Thr Ala Phe Leu Thr
1               5

<210> SEQ ID NO 92
<211> LENGTH: 9
<212> TYPE: PRT
<213> ORGANISM: artificial sequence
<220> FEATURE:
<223> OTHER INFORMATION: peptide variant of MAPK3

<400> SEQUENCE: 92

Glu His Asp Ala Thr Gly Phe Leu Thr
1               5

<210> SEQ ID NO 93
<211> LENGTH: 9
<212> TYPE: PRT
<213> ORGANISM: artificial sequence
<220> FEATURE:
<223> OTHER INFORMATION: peptide variant of MAPK3

<400> SEQUENCE: 93

Glu His Ala His Thr Gly Phe Leu Thr
1               5

<210> SEQ ID NO 94
<211> LENGTH: 9
<212> TYPE: PRT
<213> ORGANISM: artificial sequence
<220> FEATURE:
<223> OTHER INFORMATION: peptide variant of MAPK3

<400> SEQUENCE: 94

Glu Ala Asp His Thr Gly Phe Leu Thr
1               5

<210> SEQ ID NO 95
<211> LENGTH: 9
<212> TYPE: PRT
<213> ORGANISM: artificial sequence
<220> FEATURE:
<223> OTHER INFORMATION: peptide variant of MAPK3

```
<400> SEQUENCE: 95

Ala His Asp His Thr Gly Phe Leu Thr
1               5

<210> SEQ ID NO 96
<211> LENGTH: 17
<212> TYPE: PRT
<213> ORGANISM: artificial sequence
<220> FEATURE:
<223> OTHER INFORMATION: peptide variant of MAPK3

<400> SEQUENCE: 96

Ala Asp Pro Glu His Asp His Thr Gly Phe Leu Thr Glu Tyr Lys Lys
1               5                   10                  15

Lys

<210> SEQ ID NO 97
<211> LENGTH: 17
<212> TYPE: PRT
<213> ORGANISM: artificial sequence
<220> FEATURE:
<223> OTHER INFORMATION: peptide variant of MAPK3

<400> SEQUENCE: 97

Ala Asp Pro Glu His Asp His Thr Gly Phe Leu Thr Glu Tyr Lys Lys
1               5                   10                  15

Lys
```

COMPOSITIONS COMPRISING ENGINEERED PHOSPHOTHREONINE AFFINITY REAGENTS, METHODS OF MAKING, AND METHODS OF USE

This application relates to and claims the benefit of priority to U.S. provisional application Ser. No. 61/726,438, filed Nov. 14, 2012, and U.S. provisional application Ser. No. 61/604,930, filed Feb. 29, 2012, the disclosure of each of which is incorporated by reference herein.

These studies were funded by government support under 1 R01 EY016094 01A1 and 1 U54 DK093444-01 awarded by the National Institute of Health. The government has certain rights in the invention.

BACKGROUND OF THE INVENTION

1. Field of the Invention

This invention relates to the use of protein scaffolds for producing affinity reagents that specifically bind to phosphopeptides. The invention specifically relates to protein scaffolds produced from forkhead-associated domains that specifically bind to phosphopeptides comprising phosphorylated threonine amino acid residues. The invention in particular provides a plurality of phosphorylated peptide binding domains comprising libraries such as phage display libraries, methods for generating and isolating said phosphothreonine specific binding polypeptides, and methods for using said affinity reagents to monitor protein phosphorylation and study signaling events in cells.

2. Description of the Related Art

A cascade of signaling events, which involves many protein-protein interactions, is initiated within cells in response to external stimuli, including, for example, binding of a ligand to its receptor. In such cell signaling events, the signal is in many instances translocated to downstream effectors by the reversible action of protein kinases, phosphatases and phosphopeptide-binding domains. The human genome encodes for about 500 protein kinases and a third of that number of protein phosphatases (Manning et al. (2002) *Science* 298, 1912-34). Defective expression of kinases or phosphatases is the cause for various types of diseases (Cohen (2001) *Eur J Biochem* 268, 5001-10). Radioisotopic labeling studies have shown that a third of the total proteins in the cell are phosphorylated at any given time (Sefton et al. (2001) *Curr Protoc Protein Sci* Ch. 13, Unit 13 1. Phosphorylation of serine/threonine residues on proteins can lead not only to conformational changes in proteins but also create binding sites for phosphopeptide-binding domains, which play a critical role in the formation of multiprotein signaling complexes for relaying the signal to downstream signaling proteins (Yaffe et al. (2001) *Curr Opin Cell Biol* 113, 131-8). Similar to the recognition of phosphotyrosine (pY) residues by Src homology-2 (SH2) domains and phosphotyrosine binding (PTB) domains (Schlessinger et al. (2003) *Sci STKE* 2003, RE12; Yaffe (2002) *Nat Rev Mol Cell Biol* 3, 177-86), phosphorylation of serine/threonine residues creates binding sites for proteins containing phosphoserine/phosphothreonine (pS/pT)-binding domains, such as the 14-3-3 proteins (Muslin et al. (1996) *Cell* 84, 889-97; Bridges et al. (2005) *Sci STKE* 2005, RE10), tryptophan-tryptophan (WW) domain of Pin1 protein (Lu et al. (1999) *Science* 283, 1325-8), FHA domain found in prokaryotic and eukaryotic signaling proteins (Li et al. (2000) *J Cell Sci* 113 Pt 23, 4143-9; Tsai (2002) *Structure* 10, 887-8; Durocher et al. (2002) *FEBS Lett* 513, 58-66), and WD40 repeats of F-box proteins (Skowyra et al. (1997) *Cell* 91-209-19). These phosphoprotein-binding domains play a critical role in the formation of signaling complexes that eventually relay the extracellular signal downstream in the pathway. Therefore, it is evident that protein phosphorylation is a very important posttranslational modification, which is responsible for regulating proteins, translocating them to their proper subcellular location, and facilitating the formation of multiprotein complexes via protein interaction domains for transducing signals to downstream effectors and regulating processes such as gene expression, cytoskeletal rearrangements, cell cycle progression, DNA repair and apoptosis (Pawson et al. (2003)*Science* 300, 445-52; Mohammad et al. (2009) *DNA Repair (Amst)* 8, 1009-17).

Among the pS/pT-binding domains, the FHA domains are unique in that they recognize only pT containing peptides and do not show binding to either unphosphorylated threonine-containing or pS containing peptides (Durocher et al. (1999) *Mol Cell* 4, 387-94; Durocher et al. (2000) *Mol Cell* 6, 1169-82). The optimal binding motifs for various FHA domains, from *Saccharomyces cerevisiae, Schizosaccharomyces pornbe, Arabidopsis thaliana* and *Mycobacterium tuberculosis* were determined by using oriented phosphopeptide libraries that contain a fixed pT residue flanked by four degenerate residues on either side of it (Durocher et al. (2000) *Mol Cell* 6, 1169-82). From these screens, the pT +3 residue was found to be one of the major determinants of binding specificity. For example, the N-terminal FHA1 domain from *S. cerevisiae* Rad53 protein kinase prefers Asp at the pT +3 position (Liao et al. (2000) *J. Mol. Biol* 304, 941-51), the C-terminal FHA2 domain from the same protein prefers Leu/Iso at the pT+3 position (Byeon et al. (2001) *J Mol Biol* 314, 577-88) and Met/Leu/Phe at the pY +3 position (Wang et al. (2000) *J Mol Biol* 302, 927-40), and the FHA domain of the human Chk2 DNA damage check point kinase prefers Iso/Leu at the pT +3 position (Li et al. (2002) *Mol Cell* 9, 1045-54). The specificity of FHA domains ranges from recognizing singly or doubly phosphorylated sequences (Lee et al. (2008) *Mol Cell* 30, 767-78) to binding to an extended binding surface (Li et al. (2004) *J Mol Biol* 335, 371-81). From alanine-scanning experiments of the pT peptide, it was determined that the pT +3 residue contributed significantly to binding to the FHA1 domain (Durocher et al. (1999) *Mol Cell* 4, 387-94). Interestingly, non-conserved residues (G133 and G135) contribute to the pT +3 residue specificity (Yongkiettrakul et al. (2004) *Biochemistry* 43, 3862-9). The tightest FHA domain:pT peptide interaction ($k_d$=100 nM) was recently reported with structural elucidation for specific pT vs. pS recognition (Pennell et al. (2010) *Structure* 18, 1587-95).

From previous structural studies on the FHA1-pT complex from various species, it was known that amino acid residues form four loops (i.e., β3-β4, β4-β5, β6-β7, and β10-β11) make contact with the pT peptide (Durocher et al. (2000) *Mol Cell* 6, 1169-82; Pennell et al. (2010) *Structure* 18, 1587-95; Mahajan et al. (2008) *Sci Signal* 1, re12). In FHA domains from different species, the β4-β5 loop varies in sequence, structure and length. For instance, the β4-β5 loop in ChK2 FHA domain contains 19 residues with a helical insertion in the loop. The length and structure of this loop determines its positioning either close to or away from the pT +3 residue, which is an important determinant of binding specificity: these sequence differences result in specific binding to phosphopeptides with either charged (for FHA1 domain) or hydrophobic (for ChK2 FHA domain) residues in the pT +3 position. Mutating residues in the 010-011 loop has been shown to alter the binding specificity of the FHA1 domain to be more like FHA2 (Yongkiettrakul et al. (2004) *Biochemistry* 43, 3862-9) and the amino acid residues in this loop may play an important role in the binding of the FHA1 domain to a pT peptide (from Mdt1 protein) containing a hydrophobic residue at the pT +3 position (Mahajan et al. (2005) *J Am Chem Soc* 127, 14572-3). Residues from the β6-β7 loop are known to be responsible for conferring preference for binding to pT- and not pS-containing peptides (Mahajen et al. (2008) *Sci Signal* 1, re12).

Antibodies recognizing phosphorylated residues in proteins can be valuable tools for studying phosphorylation of proteins upon cellular stimulation, for instance by epidermal growth factor (EGF) or insulin, and for unraveling biologically important signal transduction pathways. Antibodies recognizing phosphorylated residues in proteins are typically generated by immunizing animals with synthetic phosphopeptides (Sun et al. (2001) *Biopolymers* 60, 61-75; Bangalore et al. (1992) *Proc Natl Acad Sci USA* 89, 11637-41). However, thousands of phosphorylation sites exist in the human proteome, so that conventional methods for generating anti-phosphopeptide antibodies would require immunization with a specific phosphopeptide for each phosphorylation site in the human proteome, making this process time consuming, expensive, laborious and impractical.

An alternative method for generating antibodies to phosphoproteins is to use recombinant methods to generate specific binding peptides or polypeptides, including antibodies in less time. For example, antibody fragments and various engineered proteins (Gebauer et al. (2009) *Curr Opin Chem Biol* 13, 245-55) have been exploited as scaffolds for generating useful affinity reagents.

SUMMARY OF THE INVENTION

The invention provides affinity reagents against phosphopeptides comprising engineered forkhead-associated domains, methods for preparing such forkhead-associated domains, and methods of using these forkhead-associated domains as affinity reagents against phosphopeptides.

In certain aspects of the invention are provided libraries of FHA variants generated by mutating residues involved in interaction with pT peptides wherein said libraries can be a source for isolating affinity reagents with new anti-phosphopeptide binding specificities different from that of the original FHA domain scaffold. Previously, it has been shown that variants of Erbin PDZ domain, generated by mutating ten residues known from structural studies to be involved in interactions with peptide ligands, had different binding specificities compared to the wild-type PDZ domain (Ernst et al. (2009) *Sci Signal* 2, ra50). This work by Ernst et al. has demonstrated that it is possible to change the specificity of a protein interaction domain to bind to a different ligand for which interaction was not previously detected.

These phosphospecific binding reagents provided by this invention are useful as tools for monitoring phosphorylation of proteins inside cells, for instance, upon stimulation with a growth factor or upon DNA damage, and as detection reagents for western blotting and immunoprecipitation experiments. For the first time, a pT binding domain has been engineered for displaying its functional variant on the surface of bacteriophage M13 and using it as a potential scaffold for generating affinity reagents to various pT peptides. This strategy can be adapted for use with various other phosphopeptide-binding domains as scaffolds for generating phosphospecific affinity reagents to pS-, pT-, and pY-containing peptides.

Additional features and advantages are described herein, and will be apparent from the following Detailed Description, Drawings and the claims.

BRIEF DESCRIPTION OF THE DRAWINGS

FIG. 1A illustrates the structure of the minor coat protein, protein III (pIII), of bacteriophage M13 containing two N-terminal domains (N1 and N2) and a C-terminal (CT) domain. Phage displaying protease sensitive protein variants between the N2 and CT domains became non-infective due to the loss of both the N-terminal domains; however, phage-displaying protease resistant variants regained their infectivity after incubation with a protease, and became enriched after several cycles of exposure to protease and amplification. FIG. 1B illustrates the structure of protein variants cleaved by proteases wherein they lost the N-terminal affinity tag so that such phage were no longer affinity captured, whereas, phage displaying protease-resistant variants were affinity captured, propagated, and enriched. FIG. 1C illustrates the structure of phage displaying variants that remained folded and active upon treatment with heat, proteases, or protein denaturants that could be isolated using a conformation-specific antibody, interacting protein, or ligand. If variants became denatured, the phage particles displaying them were lost during selection.

FIG. 2A illustrates that the coding sequence of the protein domain (PD) was amplified by mutagenic PCR (Jespers et al. (2004) *J Mol Biol* 337, 893-903). FIG. 2B illustrates subcloning of the insert DNA pool in a phage-display vector in-frame with the gene III coding sequence. FIG. 2C illustrates transformation of library DNA into *E. coli* TG1 strain that was super-infected with the helper phage M13 KO7 for phage propagation. FIG. 2D illustrates phage particle amplification overnight to produce a library of domain variants displayed as N-terminal fusions with the minor capsid protein III (pIII).

FIG. 3A shows that, before each round of biopanning, the phage library, displaying the protein domain (PD) variants, was heated at a high temperature to denature thermally unstable variants and render them non-functional. FIG. 3B shows that the heated library was cooled to room temperature and incubated with the phosphopeptide ligand immobilized on plastic via NeutrAvidin. FIG. 3C shows that the non-specifically binding phage clones were washed away using detergent. Figure D shows that the binding phage particles were eluted followed by infecting TG1 bacteria cells and super-infecting them with M13 KO7 helper phage. Figure E shows that phage clones were amplified overnight to produce the phage library. Figure F shows that the amplified phage particles were used for subsequent rounds of biopanning, and enrichment of thermally stable clones.

FIG. 4(*a*) is a graph of the results of phage ELISA demonstrating that the WT FHA1 domain and two of its variants, 3C-3S and 4C-4S, were non-functional and did not bind to the cognate pT peptide (Rad9-pT), when displayed on the surface of bacteriophage M13 as protein III fusions, whereas the D2 variant was functionally active when phage displayed. Binding of phage particles was detected using anti-M13 antibody conjugated to HRP. FIG. 4(b) is a graph of the results of ELISA experiments of GST fusions of the WT FHA1 domain and three of its variants, 3C-3S, 4C-4S, and D2, that bound specifically to the cognate pT peptide (Rad9-pT; shown as solid histograms) immobilized on plastic microtiter plate wells via Neutravidin. Binding was detected using anti-GST antibody conjugated to HRP. The peptide sequences for Rad9-pT, Rad9-T, Rad9-pS, Rad9-pY, Plk1-pT and BRCT-pS are SGSSLEVpTEADATFYAKK (SEQ ID NO: 1), SGSSLEVTEADATFYAKK (SEQ ID NO: 2), SGSSLEVpSEADATFYAKK (SEQ ID NO: 3), SGSSLEVp-YEADATFYAKK (SEQ ID NO: 4), SGSAGPMQSpTPLN-GAKK (SEQ ID NO: 5) and SGSAYDIpSQVFPFAKKK (SEQ ID NO: 6), respectively. The peptide sequence for the WT FHA1 domain from S. cerevisiae Rad53 protein kinase includes MENITQPTQQSTQATQRFLIEKFSQEQI-GENIVCRVICTTGQIPIRDLSADISQVLKEKRSIK KVWTFGRNPACDYHLGNISRLSNKHF-QILLGEDGNLLLNDISTNGTWLNGQKVEKNS NQLLSQGDEITVGVGVESDILSLVI-FINDKFKQCLEQNKVDRIRSNLKNT (SEQ ID NO:7), which includes residues 1-170 of S. cerevisiae Rad53 (SEQ ID NO:8) (Liao et al. (2000) J. Mol. Biol 304, 941-51; Durocher et al. (1999) Mol Cell 4). FIG. 4(c) shows the structures of the WT FHA1 domain (Durocher et al. (2000) Mol Cell 6, 1169-82) (PDB code: 1G6G) and three variants-4C-4S, 3C-3S and D2 prepared using PYMOL (http://www.pymol.org/) as a cartoon representation with the cysteine (C), serine (S), and phenylalanine (F) residues. The β-strands are labeled from 1 to 11 in the WT FHA1 domain structure and the N- and C-termini are noted.

FIG. 6A shows the results of phage display wherein the starting protein domains were heated at various temperatures (30° C., 40° C., 50° C., 60° C., 70° C., and 95° C.) for 3 hr and cooled to room temperature (RT). The treated and untreated (at RT) phage particles were incubated with target phosphopeptide immobilized on microtiter plate wells via NeutrAvidin. Bound phage particles were detected with anti-M13 antibody conjugated to Horseradish Peroxidase (HRP). The signal was measured at 405 nm wavelength. FIG. 6B is a graph showing similar treatment of the purified protein domain, wherein binding was detected using anti-His antibody conjugated to HRP and the signal was measured at 405 nm. The value of binding at 95° C. was equivalent to background binding of phage particles to the microtiter plate well (not shown).

FIG. 7A is a photograph of phage-displayed library heated at three different temperatures (40° C., 50° C. and 60° C.) for 3 hrs. After cooling to room temperature (RT), the untreated (at RT) and heat-treated libraries were used for screening the target phosphopeptide in the first round of selection. Phage particles bound to the target were eluted and used for infecting TG1 cells. Infected cells (10 μL) from each treatment were plated on LB/CB plates. The number of colonies represents the number of colony forming units (cfu) in the phage sample. FIG. 7B is a bar graph showing a quantitative representation of the number of colonies isolated at different temperatures after the first round of biopanning.

FIG. 9 shows the results of phage ELISA on clones recovered after three rounds of biopanning. FIG. 9A is a photograph of 96-well plates containing phage supernatants from 96 individual clones, which were isolated after three rounds of selection, heated (50° C.), cooled, and added to microtiter plate wells coated with the phosphopeptide ligand. Binding of phage particles in the wells was monitored with an anti-M13 antibody conjugated to HRP. FIG. 9B is a graph showing the ratio of the ELISA signals for individual phage clones generated with wells contained with the target protein compared to a negative control protein (background).

FIG. 13(d) is a diagram illustrating residues from the β4-β5 loop (green spheres), β6-β7 loop (orange spheres), and β10-β11 loop (red spheres) that are important for interaction with the Rad9-pT peptide, but not for folding of the FHA1 domain.

FIG. 15(a) is a graph showing binding specificity of an anti-MAPK3 affinity reagent (B1) monitored with 11 different phosphopeptide sequences and block (2% skim milk in 1×PBS), along with its cognate pT peptide (MAPK3-pT) and the non-phosphorylated form of the same peptide (MAPK3-T). FIG. 15(b) shows the percent binding of the various alanine-scanned peptide variants of MAPK3 to the anti-MAPK3 affinity reagent (B1), wherein binding to its cognate MAPK3-pT peptide is set to 100%.

FIG. 21A shows that out of the 11 alanine-scan mutants from the β4-β5 loop, the conformation of two of them (S85A and H88A) was disrupted. FIG. 21A shows that of the 5 alanine-scan mutants from the β6-β7 loop, the folding of two of them (N107A and G108A) was disrupted. FIG. 21A shows that all of the 8 alanine-scan mutants from the β10-β11 loop remained folded. The G2 variant was the original variant from which the alanine-scan variants were generated.

DETAILED DESCRIPTION OF THE PREFERRED EMBODIMENTS

Figure 1:
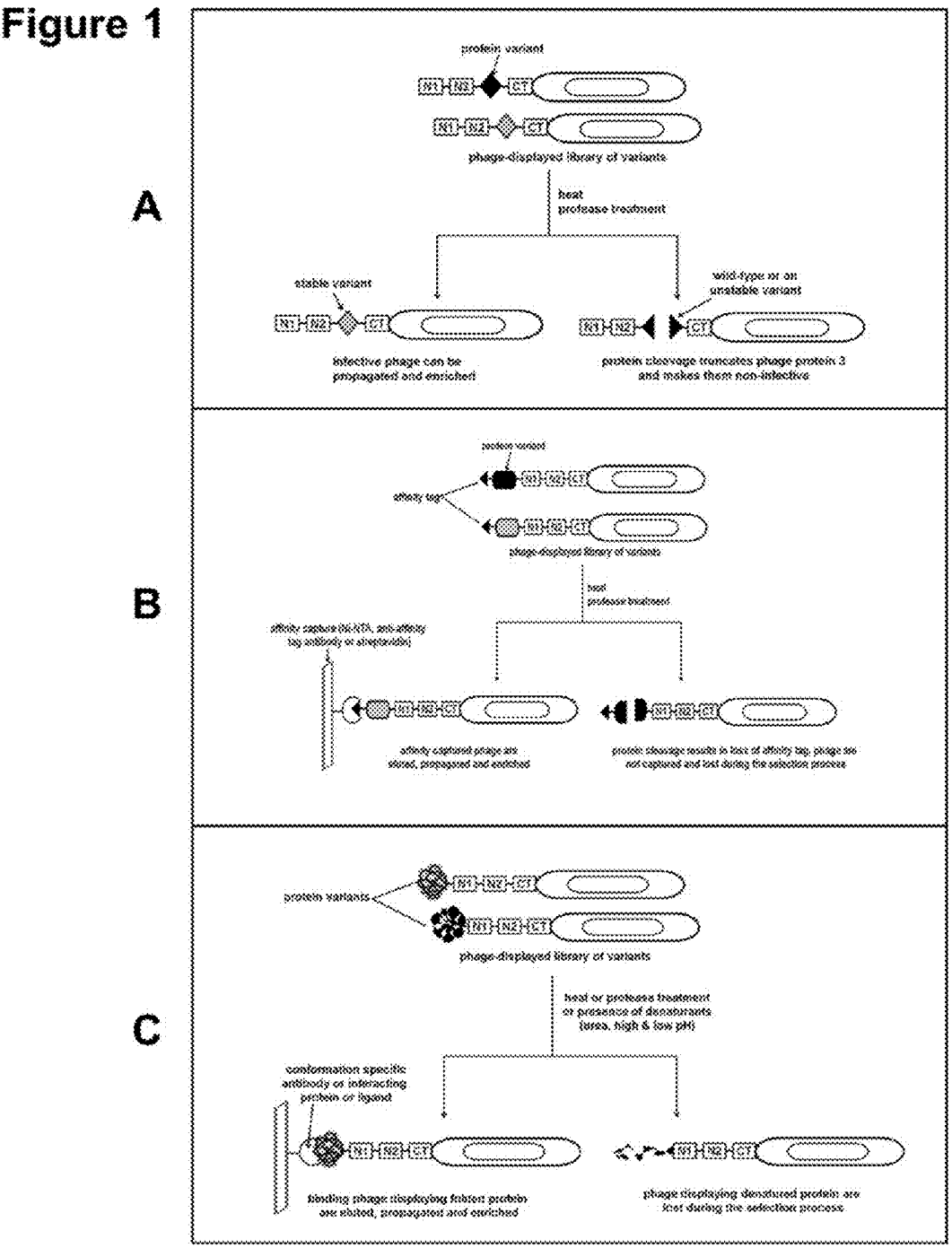
FIG. 1 is a diagrammatic representation of strategies for isolating stable proteins using selective pressure on phage particles.

The invention provides phage display libraries comprising genetically engineered variants of a protein scaffold from a phosphopeptide binding protein, to provide affinity reagents specific for peptides and polypeptides comprising a phosphothreonine residue. Other types of display, including ribosome mRNA and yeast, can also be used to generate libraries. In order to generate affinity reagents against phosphopeptides according to this invention, a wild type phosphopeptide-binding domain, e.g., a forkhead associated phosphothreonine peptide-binding domain, can be used as a scaffold to generate variants, for example, by Kunkel mutagenesis (Sidhu et al. (2000) *Methods Enzymol* 328, 333-63) or any other suitable method, and variants that bind specifically to phosphopeptides of interest can be isolated. Optionally, the phosphopeptide-binding domain can be expressed as a fusion protein to facilitate analysis of binding and for isolation. For example, the phosphopeptide-binding domain may be expressed as part of a fusion polypeptide N-terminal to a phage coat protein or in conjunction with a polypeptide sequence that facilitates expression and/or isolation, e.g., a glutathione S-transferase polypeptide, a poly-histidine tag, or the like.

The methods described herein can be used to generate libraries of phosphopeptide binding domains with members having various binding specificities for cognate phosphopeptide ligands. In a particular embodiment, an N-terminal FHA1 domain of *S. cerevisiae* Rad53 protein was used to create libraries in M13 phage. However, as one of ordinary skill in the art will appreciate, the methods disclosed may be used with any phosphopeptide binding domain, in particular FHA domains, and can be synthesized or expressed alone, or expressed as fusion proteins with a phage coat protein, including M13 phage coat proteins or other phage coat proteins, or as a fusion protein with a tag or label, e.g., a tag that facilitates isolation or a label that facilitates detection, e.g. a fluorescent, luminescent, or chromogenic label.

Creation of phage display libraries entail expression of polypeptide or antibody fragments on the surface of phage (viruses that infect bacteria), which makes it possible to isolate a single binding polypeptide or antibody fragment from a library of nonbinding clones (Marks et al. U.S. Pat. No. 6,794, 128). To express polypeptide or antibody fragments on the surface of a phage, a polypeptide or an antibody fragment gene is inserted into the gene encoding a phage surface protein, for example, pIII of bacteriophage M13, and the antibody fragment-pIII fusion protein is displayed on the phage surface. These polypeptide or antibody fragments on the surface of the phage are functional, which allows phage bearing antigen binding polypeptides or antibody fragments to be separated from non-binding phage. Isolation of specific clone is achieved by affinity selection through infecting bacteria with the eluted phage. Depending on the affinity of the polypeptide or antibody fragment, multiple rounds of affinity selection can be employed to isolate peptides that bind to specific targets.

As described in the Examples below, the N-terminal FHA1 domain of *S. cerevisiae* Rad53 protein was displayed on the surface of bacteriophage M13. This domain was initially found to be functionally inactive, i.e., unable to bind pT peptide when phage-displayed, so it was engineered to incorporate mutations that restored its binding to the pT peptide ligand when phage-displayed. The thermal stability of this functional FHA1 variant was improved by ~8° C. and residues involved in binding to the pT peptide ligand were identified by alanine-scanning. As a consequence of the application of these genetic engineering methods, the FHA1 domain was engineered for use as a scaffold protein from which novel anti-phosphospecific affinity reagents were generated.

As shown in more detail in the Examples, no binding was detected to its cognate pT peptide (Rad9-pT: SLEVpTEADATFYAKK) (SEQ ID NO:9) for wild-type (WT) FHA1 domain peptides displayed as an N-terminal fusion with capsid protein III of M13 bacteriophage. That loss of activity of the phage-displayed domain was hypothesized to be a consequence of improper folding in the oxidizing environment of the periplasm; for example, if disulfide bonds form incorrectly. The FHA1 domain has four cysteine residues (C34, C38, C74 and C154) that do not ordinarily participate in disulfide bond formation, as shown in its three-dimensional structure (Durocher et al. (2000) *Mol Cell* 6, 1169-82). Variants in which three or four of the cysteine residues were mutated to serine residues were developed and designated 3C-3S and 4C-4S, respectively. These variants remained non-functional when examined by phage ELISA (FIG. 1a). Periplasmic expression of the FHA domain was verified by detection of a Flag-epitope at the N-terminus of the phage-displayed domains. The experimental evidence thus suggested that although the FHA1 domains were being displayed, they lacked the proper conformation for ligand recognition. This finding was unexpected, because the WT FHA1 domain, and its 3C-3S and 4C-4S variants, showed specific binding to the cognate pT containing peptide (Rad9-pT: SLEVpTEADATFYAKK) (SEQ ID NO:9), when expressed in the bacterial cytoplasm as Glutathione S-transferase (GST) fusions (FIG. 1b).

Figure 17:
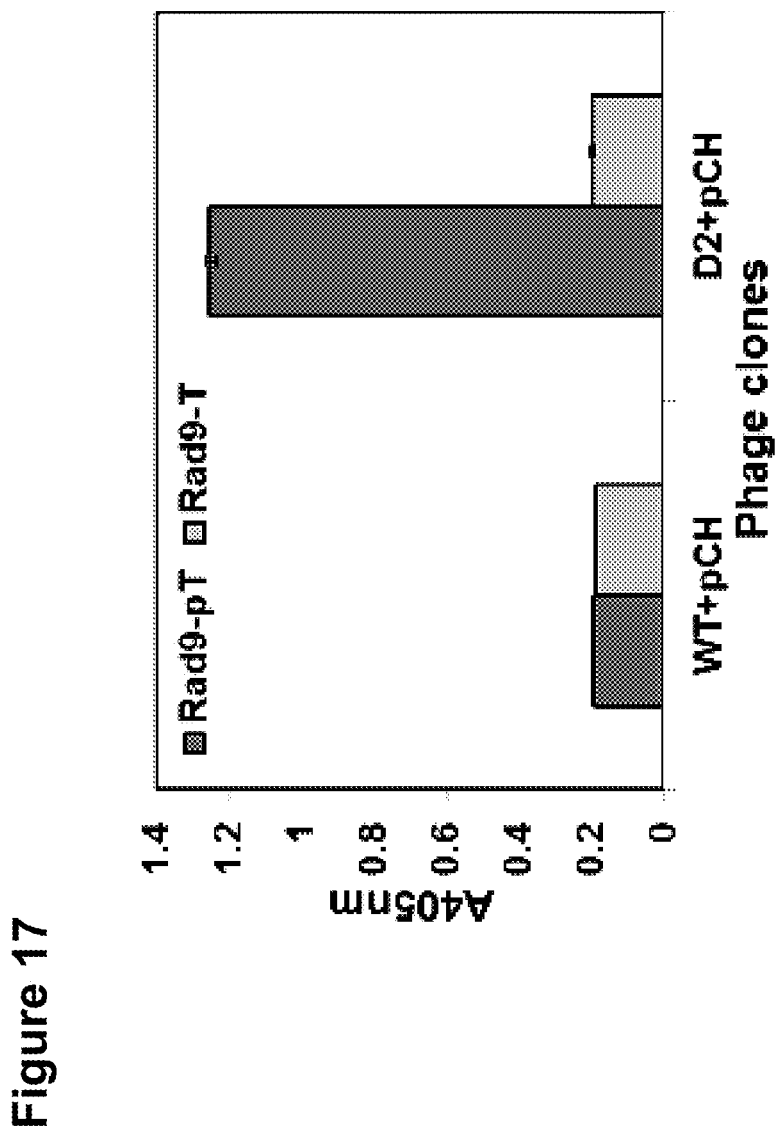
FIG. 17 is a graph showing the results of experiments expressing chaperones to aid with folding of the WT FHA1 domain in the bacterial periplasm. Five chaperones (dsbA, dsbC, fkpA, skp and surA) were expressed from the pCH vector (Schaefer et al. (2010) *Antibody engineering* (Kontermann et al.) Vol. 2, pp. 345-361. Springer-Verlag Berlin Heidelberg) and transported to the bacterial periplasm along with the FHA1 domains to facilitate with their folding. The WT domain remained nonfunctional and did not demonstrate any binding to the cognate pT peptide (Rad9-pT). The D2 variant was functional with or without the expression of chaperones (FIG. 1a).
Figure 18:
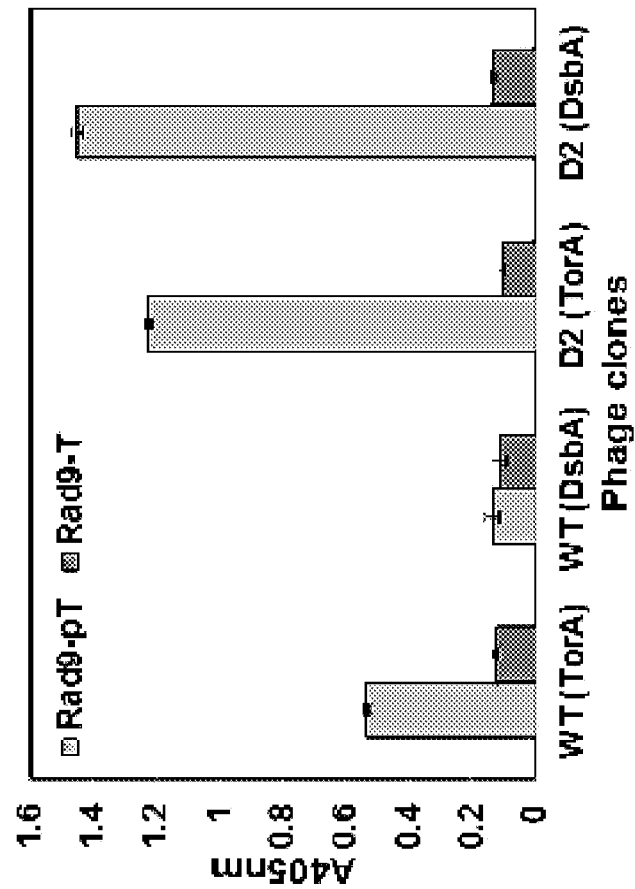
FIG. 18 is a bar graph showing the results of experiments for the effect of signal sequences on functional phage-display. The FHA domains were transported to the bacterial periplasm using two different signal sequences, the DsbA and TorA signal sequences. The WT domain was non-functional when transported via the DsbA signal sequence; however, when TorA signal sequence was used, binding to the cognate pT peptide (Rad9-pT) was only detected when the phage particles were concentrated 50 times, indicating a very low level of display. The D2 variant that was functional while using either of the signal sequences was used as a positive control; however, the phage particles needed to be concentrated ~100-fold when using the TorA signal sequence to give the same ELISA signal as the DsbA signal sequence.

To investigate whether the WT FHA1 domain could be properly phage-displayed, five chaperones that have been shown to improve folding and yields of single-chain variable fragments (SCVF) (Schaefer et al. (2010) *Antibody engineering* (Kontermann et al.) Vol. 2, pp. 345-361. Springer-Verlag Berlin Heidelberg) of antibodies were co-expressed with the phage display-encoded FHA domains. This did not restore the activity of the phage-displayed WT FHA1 domain (FIG. 17). The WT FHA1 was transported to the bacterial periplasm via the DsbA signal sequence (Schierle et al. (2010) *Antibody engineering* (Kontermann et al.) Vol. 2, p. 345-361 (Springer-Verlag Berlin Heidelberg), which transports proteins to the periplasm as they are being translated. When the WT FHA1 domain was transported to the periplasm with a different signal sequence, TorA, which transports only fully folded proteins to the periplasm (Paschke et al. (2005) *Gene* 350, 79-88; Wu e al (2000) *J Mol Microbiol Biotechnol* 2, 179-89), the activity of the phage-displayed WT FHA1 domain was only partially restored (FIG. 18).

Figure 19:
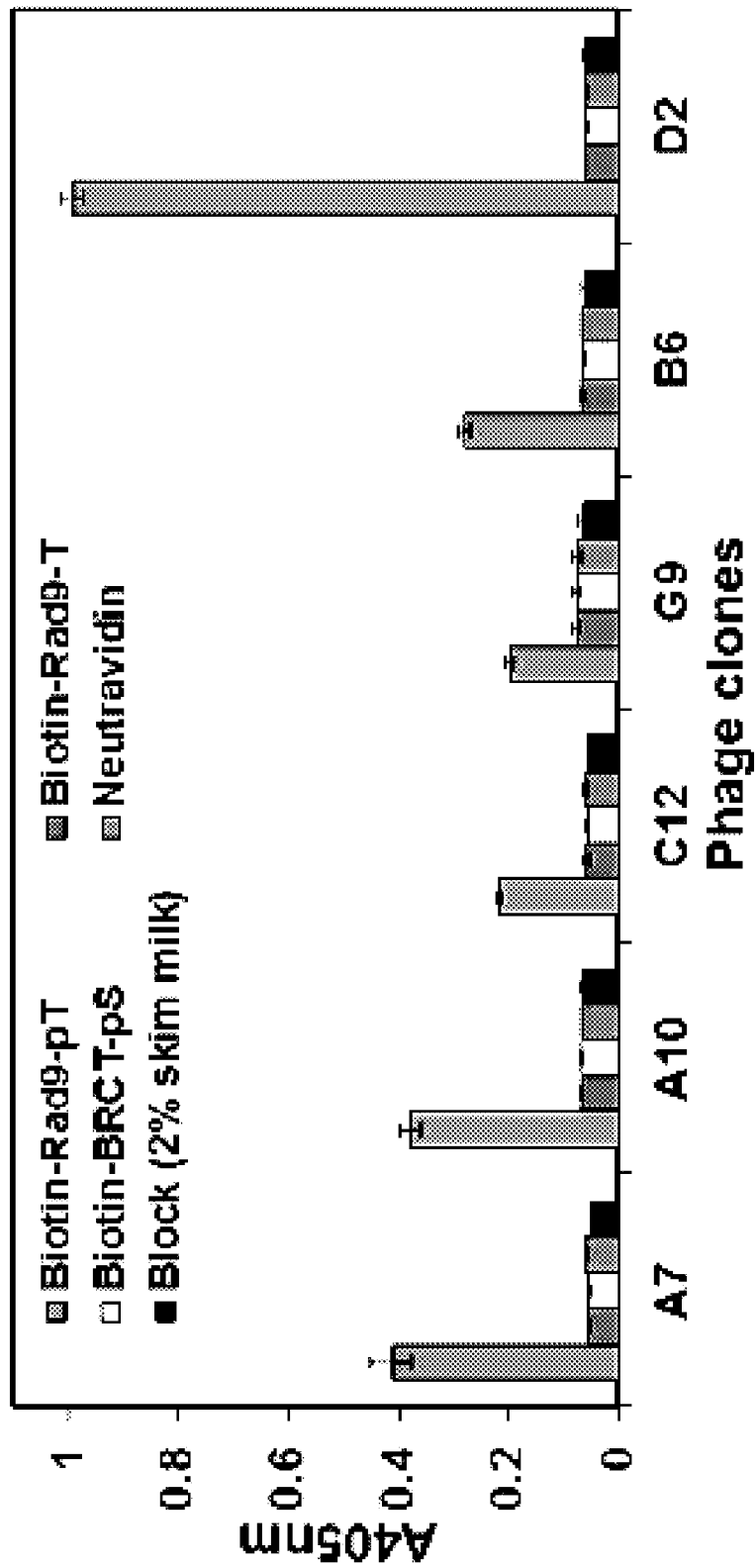
FIG. 19 is a bar graph showing phage ELISA experiments of functional FHA1 domain variants. Three rounds of affinity selection against the pT peptide (Rad9-pT: SGS-SLEVp-TEADATFYAKK) (SEQ ID NO:1), using a phage-displayed library of FHA1 variants, yielded six functional variants that specifically bound only to the cognate pT peptide (Rad9-pT) and not to any of the negative controls tested.
Figure 20:
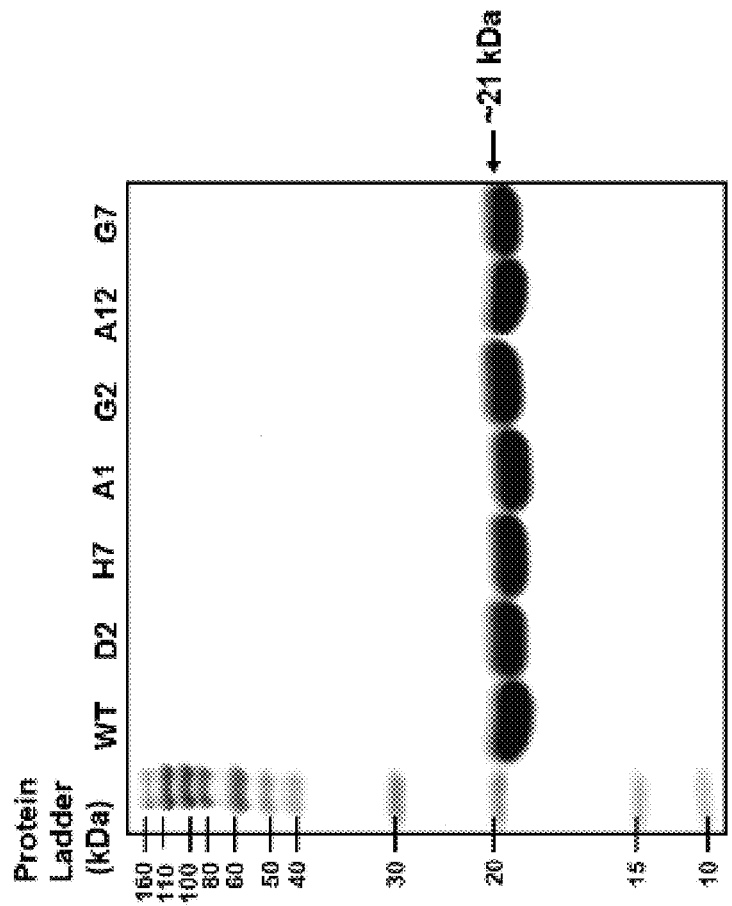
FIG. 20 is a photograph of SDS-PAGE analysis of purified FHA1 domains. The FHA1 domains were purified by IMAC via a C-terminal six-histidine tag. Purified FHA domains (4 µg) were resolved on a 15% SDS-PAGE gel, followed by staining with Coomassie Brilliant Blue. The molecular weights corresponding to protein standards are shown in kilodaltons (kDa). The FHA 1 domains are ~21 kDa in size. The protein yields per liter of culture were between 35 and 63 mg/L.

Directed evolution techniques were employed in an effort to rescue binding between phage displayed periplasmic space expressed FHA1 domains and the cognate pT containing peptide (Rad9-pT: SLEVpTEADATFYAKK) (SEQ ID NO:9). A mutagenic library comprising $2 \times 10^4$ variants of the FHA1 domain was constructed by mutagenic PCR (Cadwell et al. (1994) *PCR Methods Appl* 3, S136-40), using the 3C-3S version of the domain as the starting template. (One cysteine residue, positioned away from the binding surface, was maintained to permit embodiments immobilized to a resin by derivatization through maleimide coupling chemistry). Affinity selection of the phage library of variants with the pT peptide yielded six clones that were found to specifically bind to the phosphorylated, but not the non-phosphorylated, peptide ligand (FIG. 19). Mutations observed in the six binders are listed in Table S1. The D2 variant, which shows the strongest binding affinity to the target phosphorylated peptide, carried one mutation (S34F) in the β1 strand, suggesting that this position in the FHA domain amino acid sequence is involved in proper folding of the phage-displayed FHA1 domain.

TABLE S1

Mutations observed in the functional phage-displayed FHA1 variants isolated after three rounds of affinity selection.

| FHA domain variants[a] | Mutations | Position[b] |
|---|---|---|
| A7 | N121Y | β8-β9 loop |
| A10 | Q25H | N-terminus |
|  | N121Y | β8-β9 loop |
|  | S142R | β11 strand |
| C12 | W66R | β3 strand |

TABLE S1-continued

Mutations observed in the functional phage-displayed
FHA1 variants isolated after three rounds of affinity selection.

| FHA domain variants[a] | Mutations | Position[b] |
|---|---|---|
| G9 | Q13R | N-terminus |
|  | I104V | β6-β7 loop |
|  | N121Y | β8-β9 loop |
|  | R164S | C-terminus |
| B6 | S34A | β1-strand |
| D2 | S34F | β1-strand |

[a]FHA1 variants that specifically bind to the Rad9-pT peptide when phage-displayed.
[b]β = beta-strand. Loop is the region between two β-strands. The N-terminal mutation is present before the β1-strand and the C-terminal mutation is after the β11-strand.

Figure 5:
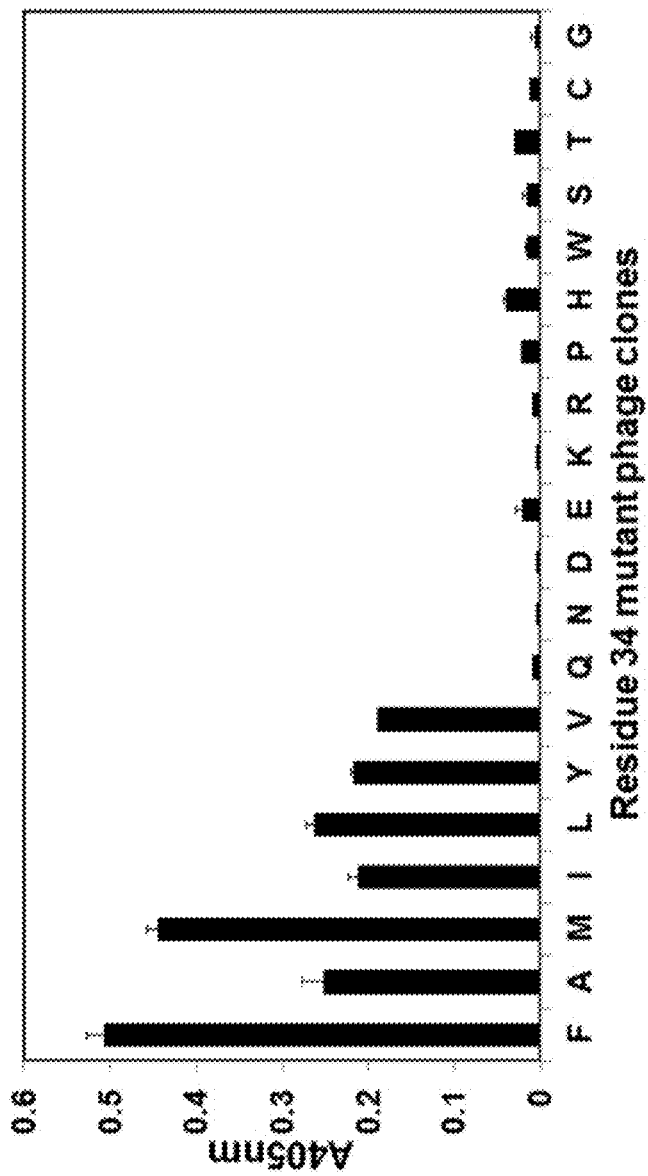
FIG. 5 is a graph showing that hydrophobic residues were preferred at position 34 for activity of phage-displayed FHA1 variants. Through Kunkel mutagenesis (Yaffe (2002) Nat Rev Mol Cell Bol 3, 177-86), the amino acid residue at position 34 in the β1 strand of the D2 FHA 1 domain was replaced (from the naturally-occurring V) one at a time with each of the other naturally occurring amino acids and binding to the immobilized Rad9-pT peptide was monitored by phage ELISA. Phage binding was detected using anti-M13 antibody conjugated to Horse Radish Peroxidase (HRP). Phage-displayed FHA1 variants containing a hydrophobic residue at position 34 (specifically, F, A, M, I, V, L and Y but not W) retained binding to the Rad9-pT. Presence of polar or hydrophilic amino acids at this position failed to rescue binding of the phage to the Rad9-pT peptide. All the variants display an N-terminal Flag peptide and the amount of phage particles used for each variant in this experiment has been normalized for this epitope.

To explore what amino acids at position 34 permitted proper folding, the D2 coding sequence was mutated one at a time to each of the other 18 natural amino acids by Kunkel mutagenesis (Sidhu et al. (2000) *Methods Enzymol* 328, 333-63). Phage ELISA showed that the FHA1 mutants bound to the pT peptide only when a hydrophobic amino acid (F, A. M, I, L, Y, and V) was present at this position with a few exceptions (W). On the other hand, hydrophilic residues at this position rendered the FHA1 variants non-functional, i.e. these mutants did not display a functional FHA1 domain (FIG. 5). Of all the 20 amino acids, the residue at position 34 that gave the highest level of binding was phenylalanine (i.e., the D2 variant).

The D2 variant with the S34F mutation was selected for further study, specifically, to identify thermal stable mutants, as described herein below. Nevertheless, the skilled worker will appreciate that any other mutant that restores folding and permits phage-displayed specific binding to the pT peptide can be used as a scaffold to develop libraries of FHA1 variants, including, but not limited to other S34 mutations (e.g., S34A, S34M, S34I, S34L, S34Y, and S34V), or other mutations correlated with restoration of specific binding to pT peptide, e.g., N121, W66, Q25, 813, 1104, and R164, and combinations thereof.

Thermal stability of the D2 variant of FHA1 bearing the S34F mutation was evaluated as set forth in the Examples below, and several mutants showing increased thermal stability were identified. It will be appreciated by the skilled worker that mutations that increase thermal stability for the D2 mutant can also enhance thermal stability of other FHA domains, e.g., in phage coat protein fusions having other FHA mutants that restore specific binding to pT peptides, in FHA domains, or fusion polypeptides comprising FHA domains linked to a polypeptide other than a phage coat protein, e.g., to GST.

Specific preferred embodiments of the invention will become evident from the following more detailed description of certain preferred embodiments and the claims. The following Examples are provided for the purposes of illustration and are not intended to limit the scope of the invention. The invention is not to be limited in scope by the exemplified embodiments, which are intended as illustrations of individual aspects of the invention. Indeed, various modifications, equivalents, and alternatives of the invention in addition to those shown and described herein will become apparent to those skilled in the art from the foregoing description and accompanying drawings. Such modifications, equivalents, and alternatives are intended to fall within the scope of the appended claims.

EXAMPLES

Example 1

Gene Synthesis and Subcloning into Phage and Expression Vectors

A variant of the FHA1 domain from the *S. cerevisiae* Rad53 protein, named the 3C-3S variant, which has three cysteine residues mutated to serine (C34S, C38S, and C154S), was commercially synthesized (Blue Heron Biotechnology) with codons optimized for expression in *E. coli* and the DNA was provided after subcloning into the Blue Heron pUC plasmid (derivative of pUC119). The 3C-3S coding sequence was amplified by polymerase chain reaction (PCR), using primers FHA1-NcoI-Fw and FHA1-NotI-Rv and the AccuPrime™ Pfx DNA polymerase (Invitrogen), for creating flanking NcoI/NotI restriction enzyme sites for subcloning into the phagemid vector (pKP600) in-frame with the gene III coding sequence. The phagemid vector (Pershad et al. (2011) *Anal Biochem* 412, 210-6) used is a modified version of the pKP300 vector except that it has a DsbA signal sequence and lacks the alkaline phosphatase coding sequence. All of the primers were ordered from Integrated DNA Technologies and their sequences are listed in Table S4.

TABLE S4

List of all the primers and their sequences used in this study.

| Primer | Sequence | Sequence ID NO |
|---|---|---|
| FHA1-BamH1-Fw | 5'-ATC ATC GGA TCC ATG GAA AAT ATT ACA CAA CCA-3' | SEQ ID NO: 10 |
| FHA1-EcoR1-Rv | 5'-GTA GAT GAA TTC GGT ATT TTT AAG ATT TGA ACG GAT ACG-3' | SEQ ID NO: 11 |
| Seq-pGEX-Fw | 5'-CAT GGC CTT TGC AGG GCT GGC AAG-3' | SEQ ID NO: 12 |
| FHA1-NcoI-Fw | 5'-TCC AGC CCA TGG CGA TGG AAA ATA TTA CAC AAC CA-3' | SEQ ID NO: 13 |
| FHA1-NotI-Rv | 5'-CGA GTC TAG ATG CGG CCG CGG TA-3' | SEQ ID NO: 14 |
| DsbA-Fw | 5'-CGCTGGCTGGTTTAGTTTTAGCGT-3' | SEQ ID NO: 15 |
| MP-FHA1-Fw | 5'-TGC TAG CGC CAT GGC GAT GGA AAA TA-3' | SEQ ID NO: 16 |
| MP-FHA1-Rv | 5'-TCG ACT GCG GCC GCG GTA TTT TTA-3' | SEQ ID NO: 17 |
| FHA1-NdeI-Fw | 5'-TAG CTA CAT ATG ACC ATG GCG ATG GAA AAT AT-3' | SEQ ID NO: 18 |
| FHA1-XhoI-Rv | 5'-GAG CTA CTC GAG GAG TGC GGC CGC GGT ATT TTT A-3' | SEQ ID NO: 19 |

TABLE S4-continued

List of all the primers and their sequences used in this study.

| Primer | Sequence | Sequence ID NO |
|---|---|---|
| pET29b-Fw | 5'-CAG CAG CCA ACT CAG CTT CCT-3' | SEQ ID NO: 20 |
| KM-S34C + S38C-FHA | 5'-GAA TTT GAC CAG TTG TGC AGA TTA CGC GGC ATA CGA TGT TTT CGC-3' | SEQ ID NO: 21 |
| KM-S154C-FHA | 5'-GAC TTT ATT TTG TTC CAG GCA TTG TTT GAA TTT ATC G-3' | SEQ ID NO: 22 |
| KM-C74S-FHA1 | 5'-ACC TAA GTG ATA ATC AGA GGC TGG GTT ACG TCC A-3' | SEQ ID NO: 23 |
| F-TAA | 5'-TGT TGA GAT TAC GCG TTA TAC GAT GTT TTC GC-3' | SEQ ID NO: 24 |
| F-Leu | 5'-TGT TGA GAT TAC GCG CAG TAC GAT GTT TTC GC-3' | SEQ ID NO: 25 |
| F-Ile | 5'-TGT TGA GAT TAC GCG AAT TAC GAT GTT TTC GC-3' | SEQ ID NO: 26 |
| F-Met | 5'-TGT TGA GAT TAC GCG CAT TAC GAT GTT TTC GC-3' | SEQ ID NO: 27 |
| F-Val | 5'-TGT TGA GAT TAC GCG AAC TAC GAT GTT TTC GC-3' | SEQ ID NO: 28 |
| F-Pro | 5'-TGT TGA GAT TAC GCG CGG TAC GAT GTT TTC GC-3' | SEQ ID NO: 29 |
| F-Thr | 5'-TGT TGA GAT TAC GCG GGT TAC GAT GTT TTC GC-3' | SEQ ID NO: 30 |
| F-Ala | 5'-TGT TGA GAT TAC GCG TGC TAC GAT GTT TTC GC-3' | SEQ ID NO: 31 |
| F-Tyr | 5'-TGT TGA GAT TAC GCG ATA TAC GAT GTT TTC GC-3' | SEQ ID NO: 32 |
| F-His | 5'-TGT TGA GAT TAC GCG GTG TAC GAT GTT TTC GC-3' | SEQ ID NO: 33 |
| F-Asn | 5'-TGT TGA GAT TAC GCG GTT TAC GAT GTT TTC GC-3' | SEQ ID NO: 34 |
| F-Lys | 5'-TGT TGA GAT TAC GCG TTT TAC GAT GTT TTC GC-3' | SEQ ID NO: 35 |
| F-Asp | 5'-TGT TGA GAT TAC GCG ATC TAC GAT GTT TTC GC-3' | SEQ ID NO: 36 |
| F-Glu | 5'-TGT TGA GAT TAC GCG TTC TAC GAT GTT TTC GC-3' | SEQ ID NO: 37 |
| F-Cys | 5'-TGT TGA GAT TAC GCG ACA TAC GAT GTT TTC GC-3' | SEQ ID NO: 38 |
| F-Trp | 5'-TGT TGA GAT TAC GCG CCA TAC GAT GTT TTC GC-3' | SEQ ID NO: 39 |
| F-Arg | 5'-TGT TGA GAT TAC GCG ACG TAC GAT GTT TTC GC-3' | SEQ ID NO: 40 |
| F-Gly | 5'-TGT TGA GAT TAC GCG GCC TAC GAT GTT TTC GC-3' | SEQ ID NO: 41 |
| F-Glu | 5'-TGT TGA GAT TAC GCG CTG TAC GAT GTT TTC GC-3' | SEQ ID NO: 42 |
| KM-G2-L78A | 5'-GCG GCT AAT GTT ACC CGC GTG ATA ATC GCA GGC-3' | SEQ ID NO: 43 |
| KM-G2-G79A | 5'-GCG GCT AAT GTT CGC TAA GTG ATA ATC GC-3' | SEQ ID NO: 44 |
| KM-G2-N80A | 5'-AGA TAA GCG GCT AAT CGC ACC TAA GTG ATA ATC-3' | SEQ ID NO: 45 |
| KM-G2-I81A | 5'-ATT AGA TAA GCG GCT CGC GTT ACC TAA GTG ATA-3' | SEQ ID NO: 46 |
| KM-G2-S82A | 5'-GTG TTT ATT AGA TAA GCG CGC AAT GTT ACC TAA GTG AT-3' | SEQ ID NO: 47 |
| KM-G2-R83A | 5'-GAA AGT GTT TAT TAG ATA ACG CGC TAA TGT TAC CTA AGT GA-3' | SEQ ID NO: 48 |
| KM-G2-L84A | 5'-GTG TTT ATT AGA CGC GCG GCT AAT GTT ACC T-3' | SEQ ID NO: 49 |
| KM-G2-S85A | 5'-GAT TTG AAA GTG TTT ATT CGC TAA GCG GCT AAT GTT AC-3' | SEQ ID NO: 50 |
| KM-G2-N86A | 5'-GAG GAT TTG AAA GTG TTT CGC AGA TAA GCG GCT AAT GT-3' | SEQ ID NO: 51 |
| KM-G2-K87A | 5'-CAG GAG GAT TTG AAA GTG CGC ATT AGA TAA GCG GCT AAT-3' | SEQ ID NO: 52 |
| KM-G2-H88A | 5'-GCC CAG GAG GAT TTG AAA CGC TTT ATT AGA TAA GCG GCT-3' | SEQ ID NO: 53 |
| KM-G2-G133A | 5'-ATC GCT TTC TAC ACC TAC CGC TAC CGT AAT TTC GTC GC-3' | SEQ ID NO: 54 |
| KM-G2-V134A | 5'-ATA TCG CTT TCT ACA CCC GCG CCT ACC GTA ATT CGT C-3' | SEQ ID NO: 55 |
| KM-G2-G135A | 5'-TAT CGC TTT CTA CCG CTA CGC CTA CCG TA-3' | SEQ ID NO: 56 |
| KM-G2-V136A | 5'-ATA TCG CTT TCC GCA CCT ACG CCT ACC G-3' | SEQ ID NO: 57 |

TABLE S4-continued

List of all the primers and their sequences used in this study.

| Primer | Sequence | Sequence ID NO |
|---|---|---|
| KM-G2-E137A | 5'-GCTTAAAATATCGCTCGCTACACCTACGCCTAC-3' | SEQ ID NO: 58 |
| KM-G2-S138A | 5'-GCT TAA AAT ATC CGC TTC TAC ACC TAC GCC-3' | SEQ ID NO: 59 |
| KM-G2-D139A | 5'-GAC TAA GCT TAA AAT CGC GCT TTC TAC ACC TAC-3' | SEQ ID NO: 60 |
| KM-G2-I140A | 5'-ATG ACT AAG CTT AAC GCA TCG CTT TCT ACA CCT A-3' | SEQ ID NO: 61 |
| KM-G2-I104A | 5'-GCC ATG TAC CAT TTG TTG ACG CGT CGT TGA GTA ATA AGT-3' | SEQ ID NO: 62 |
| KM-G2-S105A | 5'-GAG CCA TGT ACC ATT TGT CGC GAT GTC GTT GAG TAA TA-3' | SEQ ID NO: 63 |
| KM-G2-T106A | 5'-TGA GCC ATG TAC CAT TCG CTG AGA TGT CGT TGA GTA-3' | SEQ ID NO: 64 |
| KM-G2-N107A | 5'-CGT TGA GCC ATG TAC CCG CTG TTG AGA TGT CGT TGA G-3' | SEQ ID NO: 65 |
| KM-G2-G108A | 5'-TGA CCG TTG AGC CAT GTC GCA TTT GTT GAG ATG TCG T-3' | SEQ ID NO: 66 |
| β4-β5 Lib | 5'-CCC AGG AGG ATT TGA AAG TGT TTA TTA GAK NNK NNK NNA ATG TTA CCT AAG TGA TAA TCG CAG GC-3' | SEQ ID NO: 67 |
| β10-β11 Lib | 5'-GTT TGA ATT TAT CGT TAA TAA AAA TGA CTA AGC TTA AAA TKN NKN NKN NKN NKN NKN NKN NTA CCG TAA TTT CGT CGC CTT GA-3' | SEQ ID NO: 68 |
| pKP700-G2-XmaI#1 | 5'-CCA GGA GGA TTT GAA AGT GTT TAT TAG ACC CGG GGC TAA TGT TAC CTA AGT GAT AAT CGC AG-3' | SEQ ID NO: 69 |
| pKP700-G2-XmaI#2 | 5'-CGT TAA TAA AAA TGA CTA AGC TTA AAA TAT CGC TTT CCC GGG GTA CGC CTA CCG TAA TTT CGT CG-3' | SEQ ID NO: 70 |
| Phos β4-β5 Lib | /5Phos/CCC AGG AGG ATT TGA AAG TGT TTA TTA GAK NNK NNK NNA ATG TTA CCT AAG TGA TAA TCG CAG GC-3' | SEQ ID NO: 71 |
| Phos β10-β11 | /5Phos/GTT TGA ATT TAT CGT TAA TAA AAA TGA CTA AGC TTA AAA TKN NKN NKN NKN NKN NKN NKN NTA CCG TAA TTT CGT CGC CTT GA-3' | SEQ ID NO: 72 |

Following the protocol for Kunkel mutagenesis (Sidhu et al. (2000) *Methods Enzymol* 328, 333-63), the WT FHA1 domain (containing four cysteine residues at positions 34, 38, 74, and 154) was generated using the 3C-3S coding sequence as the template and two oligonucleotides; the first oligonucleotide (KM-S34+S38C-FHA1) mutated S34 and S38 to cysteine, and the second oligonucleotide (KM-S154C-FHA1) converted position S154 serine to cysteine. Another FHA1 variant, 4C-4S (all four cysteines mutated to serines) was generated from the 3C-3S variant using one oligonucleotide (KM-C74S-FHA1), which mutated position 74 cysteine to serine. All the phagemid vectors were sequenced using the primer DsbA-Fw. For generating GST fusions of the FHA1 domains for cytoplasmic expression, their coding sequence was amplified by PCR creating BamHI/EcoRI flanking sites using the primers FHA1-BamHI-Fw and FHA1-EcoRI-Rv and AccuPrime™ Pfx DNA polymerase. The pGEX-2T GST fusion vector (GE Healthcare) was cut with the same two restriction endonucleases and the FHA1 domains were sub-cloned in-frame with the GST coding sequence. The final construct was sequenced using the primer Seq-pGEX-Fw. All of the restriction enzymes were purchased from New England BioLabs.

For expression on a large scale, the FHA domains were subcloned into a modified version of the pET29b expression vector (gift from Brian Kuhlman, University of North Carolina) in-frame with a C-terminal six-histidine tag for protein purification by immobilized metal affinity chromatography (IMAC). The FHA1 domain coding sequences were amplified by PCR using the AccuPrime™ Pfx DNA polymerase and FHA1-NdeI-Fw and FHA1-XhoI-Rv primers, which created flanking NdeI/XhoI restriction sites for sub-cloning into the pET29b expression vector for cytoplasmic expression. The final constructs were sequenced using the pET29b-Fw primer.

Example 2

Construction of Phage-Displayed Libraries

To generate a library of FHA1 variants, from which functional phage-displayed variants can be isolated by affinity selection, mutagenic PCR (Cadwell et al. (1994) *PCR Methods Appl* 3, S136-40) was performed (primers: MP-FHA1-Fw and MP-FHA1-Rv), using the coding sequence of the 3C-3S variant as the starting template. One cysteine remained, which was away from the binding surface, so that it could be derivatized through maleimide coupling chemistry for future immobilization to resin. Mutagenic PCR was performed to amplify and generate mutations randomly across the coding region of the 3C-3S variant. This method (Elia et al. (2003) *Cell* 115, 83-95) generates an error rate of 0.66% per position and the estimated mutants in the library are ~4% wild-type, 12%, 20%, 22%, 18%, and 12%, with 1-5 mutations, respectively, and 12% with 6 or more mutations. From sequencing 30 clones chosen at random from the library, it was observed that the numerical distribution of mutations in the library matched the predictions. The insert DNA pool (~0.34 µg) was digested with NcoI/NotI enzymes, and subcloned into a phagemid vector (pKP600, ~1 µg), which was cut with the same restriction sites, generating in-frame fusions with the gene III coding sequence at the C-terminus and a FLAG epitope tag at the N-terminus. The recombinant DNA was concentrated using a Phenol:Chloroform:Isoamyl alcohol mixture (Sigma), and transformed into TG1 bacterial cells. The cells were recovered by shaking at 250 rpm at 37° C. for 40 min and various dilutions (10 μL and 100 μL of $10^{-1}$ and $10^{-2}$) were plated on LB agar (100 mm×15 mm). The remaining cells were plated on three LB agar plates (150 mm×15 mm) containing 50 μg/mL carbenicillin. The next day, colonies were counted on the titration plates and the library diversity was determined to be $2\times10^4$ clones. The bacterial lawn on large plates was scraped, 30 mL of LP/carbenicillin media was inoculated with ~$1\times10^8$ cells and grown to mid-log ($OD_{600nm}$=0.5) followed by infection with M13KO7 helper phage (MOI=20) for 1 h at 37° C. at low speed (150 rpm). Infected cells were collected by centrifugation, resuspended in 30 mL of fresh LP media containing carbenicillin and kanamycin (50 μg/mL) and incubated overnight at 30° C. with shaking at 250 rpm. The next day, phage particles were precipitated using ⅕ volume of 24% polyethylene glycol (PEG) and 3 M NaCl mixture, the phage pellet was resuspended in PBS (1 mL), and stored in aliquots at −80° C. with 16% final glycerol concentration. Similarly, another mutagenic library was constructed, with a final diversity of $6\times10^7$ variants, using the D2 variant coding sequence as the starting template.

Example 3

Construction of Phage-Displayed Libraries by Oligonucleotide-Directed Mutagenesis 1. FHA1G2 Library For constructing site-directed libraries of FHA1 variants, the pKP700 vector with the FHA1G2 coding sequence was used as the starting template. Eight residues (L78, R83, L84 from the β4-β5 loop and G133, V134, G135, V136, D139 from the β10-β11), in the FHA1G2 coding sequence were randomized based on our alanine-scanning results. Following Kunkel mutagenesis protocol (Sidhu et al. (2000) *Methods Enzymol* 328, 333-63), two oligonucleotides (β4-β5 NNK and β10-β11 NNK, 5' phosphorylated) with NNK codons (N=A, G, C, or T; K=G or T) at these 8 positions were annealed to the single-stranded uracilated phagemid DNA (pKP700) at a molar ratio of 1:5 (single-stranded DNA:oligonucleotides), extended using T7 DNA polymerase and the covalently closed circular DNA was sealed by T4 DNA ligase (both from New England BioLabs). A total of 15 transformations were done into electrocompetent TG1 bacterial cells (Lucigen Corporation). After recovery, the cells were pooled, plated on three 15 cm 2×YT/CB agar plates, and incubated overnight at 30° C. The lawn of colonies were scraped with a total of 6 mL of freezing media (2×YT/CB/16% glycerol) media and the library cells were stored at −80° C.

Example 4

Construction of Phage-Displayed Libraries by Oligonucleotide-Directed Mutagenesis 2. G2-XmaI Library A second library (G2-XmaI) was constructed, using two oligonucleotides (Phos β4-β5 Lib and Phos β10-β11 Lib, 5' phosphorylated) randomized at a total of 10 positions (S82, R83, L84 from the β4-β5 loop, and G133, V134, G135, V136, E137, S138, D139 from the β10-β11) with NNK codons. S82 was randomized in this library, because it was shown to make contacts with the pT peptide from previously structural studies (Durocher et al. (2000) *Mol Cell* 6, 1169-82). L78 was excluded because preliminary affinity selection results revealed that many binding clones retained Leu at this position. E137 and S138 were randomized to facilitate efficient annealing of the oligonucleotide to the template DNA, however, according to alanine-scanning results, these residues were not important for binding to the pT peptide. The pKP700 phagemid DNA used for constructing this library has two Xma I restriction sites, one in the β4-β5 loop and the second one in the β10-β11 loop, introduced by Kunkel mutagenesis, using primers pKP700-G2-XmaI#1 and pKP700-G2-XmaI#2. The G2-XmaI library consisted of four sub-libraries, each with a diversity of ~$5\text{-}7\times10^9$ members. Each sub-library was constructed by performing 25 transformations into electrocompetent TG1 cells (total of ~$2.5\times10^9$ transformants). The recovered cells were pooled, grown to an $OD_{600nm}$=1.0 ($10^9$ cells/mL), and phagemid DNA was purified from half the number of cells ($3\times10^{11}$ cells) using the PureLink™ HiPure Plasmid Filter Maxiprep Kit (Invitrogen). The DNA (10 μg) was cut with Xma I restriction enzyme (5 units/μg of DNA) for 16 h/37° C. The cut DNA was purified using one QIAquick® PCR Purification Kit (Qiagen), 10 transformations were done into electrocompetent TG1 cells (total of ~$5\text{-}7\times10^9$ transformants), and after recovery, the cells were plated on ten 15 cm 2×YT/CB agar plates. The next day, colonies were scraped with a total of 40 mL of freezing media and the library cells were stored at −80° C.

Example 5

Amplification of the FHA1G2 and G2-XmaI Libraries

For amplifying the library phage, 2×YT/CB media was inoculated with sufficient number of scraped cells (to cover 10× the library diversity), grown to mid-log phase (infect 10× the library diversity number of cells; $4\times10^8$ cells/mL at mid-log), and infected with the trypsin cleavable helper phage (TM13KO7, $10^{10}$ pfu/mL) for 1 h at 37° C./150 rpm. Infected cells, recovered after centrifugation, were resuspended in fresh 2×YT/CB/Kan medium (10 times the initial volume) and phage were amplified for 18-19 h at 30° C., with 250 rpm shaking Phage were concentrated 100 fold by PEG/NaCl precipitation, filtered through 0.45 μm syringe filters, glycerol was added to a final concentration of 16%, and the phage library was stored at −80° C. For the four sub-libraries, phage was amplified from each library separately and pooled before performing affinity selections with various pT-containing peptides.

Example 6

Affinity Selection Against Various Phosphothreonine Peptides

Dynabeads® MyOne™ Streptavidin T1 magnetic beads (Invitrogen Dynal AS, 100 μL) were incubated with the biotinylated pT peptide (1.2 μg; 1.5 μM concentration) for 30 min. All the selection steps were performed at room temperature. The unbound target was removed and the beads were blocked for 1 h with blocking buffer (2% skim milk in PBS with 1 μM free biotin; 1 mL). The phage library ($3\times10^{12}$ phage) was incubated for 15 min with equal volume of 4% skim milk in PBS, and then added to the blocked beads. Washing the beads three times with PBST and twice with PBS minimized non-specific binding of phage particles to the beads. Phage bound to the target were eluted using TPCK treated trypsin (Sigma-Aldrich, 400 µL at 100 µg/mL concentration) and used to infect 800 µL of TG1 cells at mid-log growth phase ($OD_{600nm}$=0.5) for 40 min at 37° C. The cells were then plated on one 15 cm 2×YT/CB agar plate and the colonies were scraped the next day with 8 mL of freezing media. For amplifying the phage for the second round of selection, ~$10^8$-$10^9$ cells were inoculated into 40 mL of 2×YT/CB media, grown to mid-log, and 5 mL was infected with trypsin cleavable helper phage (TM13KO7; $10^{10}$ pfu/mL). The infected cells, after centrifugation, were resuspended in 30 mL of 2×YT/CB/Kan media, phage were amplified overnight at 30° C./250 rpm and precipitated (30 fold) with PEG/NaCl mixture. The second round of affinity selection was conducted in the same manner, except that more number of washes were done before eluting the bound phage (five times with PBST and three times with PBS) and after infecting TG1 cells at mid-log with eluted phage, 10 µL and 100 µL of $10^{-2}$ and $10^{-4}$ dilutions were plated on 2×YT/CB agar plates (10 cm). After the second round of affinity selection, 96 individual clones were propagated as phage, followed by phage ELISA to identify functional clones that recognize the pT peptide ligand, and positive binding clones were sequenced.

It should be understood that the foregoing disclosure emphasizes certain specific embodiments of the invention and that all modifications or alternatives equivalent thereto are within the spirit and scope of the invention as set forth in the appended claims.

Example 7

Affinity Selection

For isolating functional, phage-displayed FHA1 variants, three rounds of affinity selection were performed against the pT peptide ligand (SLEVpTEADATFYAKK) (SEQ ID NO:9) using the phage-displayed library that was generated by mutagenic PCR. All the selection steps were performed at room temperature. The biotinylated peptide (200 µL, 10 µg/mL) was immobilized on a Nunc polystyrene tube (Thermo Fisher Scientific) via NeutrAvidin™ Biotin binding protein (200 µL, 20 µg/mL; Thermo Fisher Scientific) and blocked with 2% skim milk in 1×PBS. Then, the phage library (~1×$10^{10}$ phage particles) was incubated with the blocked target for 1 h, followed by six washes with PBST and six washes with PBS. Phage particles bound to the target were eluted using 100 mM glycine-HCl (100 µL; pH 2.0), neutralized with 2 M Tris-base (6 µL; pH 10.0) and used to infect 800 µL of TG1 cells at mid-log ($OD_{600nm}$=0.5) for 40 min at 37° C. The cells were plated after infection, scraped the next day, and the phage was amplified and precipitated as described above. The second and third rounds of affinity selection were conducted in the same manner, except that only ½ of the volume of the eluted phage was used to infect bacterial cells after round 2 and ¼ of the volume was used in round 3. After the third round of affinity selection, 96 individual clones were propagated as phage, followed by phage ELISA to identify functional clones that recognize the pT peptide ligand. Positive binding clones were sequenced, and further specific tests were performed.

Example 8

Protein and Phage Enzyme-Linked Immunosorbent Assay

To amplify the phage particles displaying the recombinant FHA1 variants, TG1 bacterial cells (5 mL; Stratagene) har-boring the phagemid DNA were infected at mid-log ($OD_{600nm}$=0.5-0.6) with M13K07 helper phage (New England Biolabs) at a multiplicity of infection (MOI) of 20 for 1 h at 37° C. at 150 rpm. Infected cells were centrifuged, and the pellet was resuspended in fresh Luria Bertani medium (LB: 10 g Tryptone, 5 g Yeast extract, and 10 g NaCl per liter) supplemented with 50 µg/mL carbenicillin and 50 µg/ml kanamycin, and phage were amplified overnight at 30° C. at 250 rpm. All of the phage ELISA steps were performed at room temperature. Biotinylated peptides (100 µL, 5 µg/mL) were immobilized on Nunc MaxiSorp flat-bottom 96 well plates (Thermo Fisher Scientific) via NeutrAvidin™ Biotin binding protein (100 µL, 10 µg/mL; Thermo Fisher Scientific) and blocked with 2% skim milk in 1×PBS (200 µL per well). After washing with Phosphate Buffered Saline (PBS: 0.14 M Sodium Chloride, 0.003 M Potassium Chloride, 0.002 M Potassium Phosphate, and 0.01 M Sodium Phosphate), the wells were incubated with the phage supernatant (100 µL of phage diluted 1:2 with PBS containing 0.1% Tween 20 (PBST)) for 1 h and washed three times with PBST. The binding phage were detected using anti-M13 antibody conjugated to horse radish peroxidase (HRP) (GE Healthcare) diluted 1:5000 with PBST. After washing away the unbound antibody, the chromogenic substrate for HRP; 2,2'-Azinobis (3-ethylbenzothiazoline-6-Sulfonic Acid) diammonium salt (Thermo Fisher Scientific), supplemented with hydrogen peroxide was added (100 µL per well), and the absorbance of the green colored complex was measured at 405 nm on POLARstar OPTIMA microtiter plate reader (BMG Labtech).

For production of FHA1-GST fusion protein, BL21 DE3 cells (10 mL; Stratagene) harboring the expression vector was grown overnight at 30° C. using the Overnight Express™ Autoinduction System 1 (Novagen). The next day, cells were lysed using BugBuster® 10× Protein Extraction Reagent (Novagen) following the manufacturer's instructions. Cell lysate (100 µL diluted 1:5 with PBST) was incubated with the biotinylated peptides as described above and detected using anti-GST antibody conjugated to HRP (diluted 1:10,000 with PBST; GE Healthcare).

Example 9

Peptides

Peptides were synthesized at the Research Resource Center, University of Illinois at Chicago and were >90% purity. All the peptides, except for the one used for isothermal titration calorimetry (ITC), were biotinylated at their N-terminus, and amidated at their C-terminus. The peptide used for ITC is SLEVpTEADATFYAKK (SEQ ID NO:9) (Durocher et al. (2000) Mol Cell 6, 1169-82). It was purified by HPLC and does not contain a linker and N- or C-terminal modifications. In several experiments, the peptides contained a tripeptide spacer, SerGlySer (SGS), between the N-terminal biotin and the peptide sequence, and often required the addition of two or three lysine residues at the C-terminus to increase their solubility. The peptides used for affinity selection experiments did not contain the tripeptide spacer because we did not want it to potentially be part of the FHA1 domain binding 'epitope'. However, the peptides used to confirm binding in ELISA experiments did have the SGS linker, between the N-terminal biotin and the target peptide sequence. The phosphopeptide sequences, with their SGS linkers, are as follows: Rad9-pT: SGS-SLEVpTEADATFYAKK (SEQ ID NO:1) (Durocher et al. (2000) Mol Cell 6, 1169-82); Rad9-pS: SGS-SLEVpSEADATFYAKK (SEQ ID NO:3); Rad9-pY: SGS- SLEVpYEADATFYAKK (SEQ ID NO:4); Plk1-pT: SGS-AGPMQSpTPLNGAKK (SEQ ID NO:5) (Elia et al. (2003) *Cell* 115, 83-95), BRCT-pS: SGS-AYDIpSQVFPFAKKK (SEQ ID NO:6) (Williams et al. (2004) *Nat Struct Mol Biol* 11, 519-25). All the other phosphopeptides, whose sequences are obtained from phosida.com (posttranslational modification database) website, are listed in Table S5 and they do not contain the SGS linker.

TABLE S5

List of peptides and their sequences from phosida.com

| Accession# | Protein | Phosphosite | Sequence | SEQ ID NO |
|---|---|---|---|---|
| IPI00003479 | Mitogen-activated protein kinase 1 | MAPK1-pT(185) | HDHTGFLpTEYVATKK | SEQ ID NO: 73 |
| IPI00018195 | Mitogen-activated protein kinase 3 | MAPK3-pT(197)<br>MAPK3-pY(203) | ADPEHDHpTGFLTEYKKK<br>HTGFLTEpYVATRWYR | SEQ ID NO: 74<br>SEQ ID NO: 75 |
| IPI00013439 | Transcription factor jun-B | JunB-pT(255) | EARSRDApTPPVSPYKK | SEQ ID NO: 76 |
| IPI00234446 | Activating transcription factor 2 | ATF2-pTpT(69, 71) | IVADQpTPpTPTRFLKY | SEQ ID NO: 77 |
| IPI00289547 | Transcription factor jun-D | JunD-pT(245) | ALKDEPQpTVPDVPYKKK | SEQ ID NO: 78 |
| IPI00796046 | Transcription factor Myc | Myc-pT(58) | KKFELLPpTPPLSPSY | SEQ ID NO: 79 |
| IPI00165135 | Src homology 2 domain containing transforming protien 1 | Shc1-pT(35) | GSFVNKPpTRGWLHKK | SEQ ID NO: 80 |
| IPI00018274 | Isoform 1 of Epidermal growth factor receptor precursor | EGFR-pT(993)<br>EGFR-pY1(998)<br>EGFR-pY2(1092) | RMHLPSPpTDSNFYRA<br>SPTDSNFpYRALMDKK<br>TFLPVPEpYINQSVKK | SEQ ID NO: 81<br>SEQ ID NO: 82<br>SEQ ID NO: 83 |
| IPI00017305 | Ribosomal protein S6 kinase alpha-1 | RSKA1-pT(359) | DTEFTSRpTPKDSPYKK | SEQ ID NO: 84 |
| IPI00003783 | Dual specificity mitogen-activated protein kinase kinase 2 | MAP2K2-pT(394) | LRLNQPGpTPTRTAYKK | SEQ ID NO: 85 |

Example 10

Figure 13:
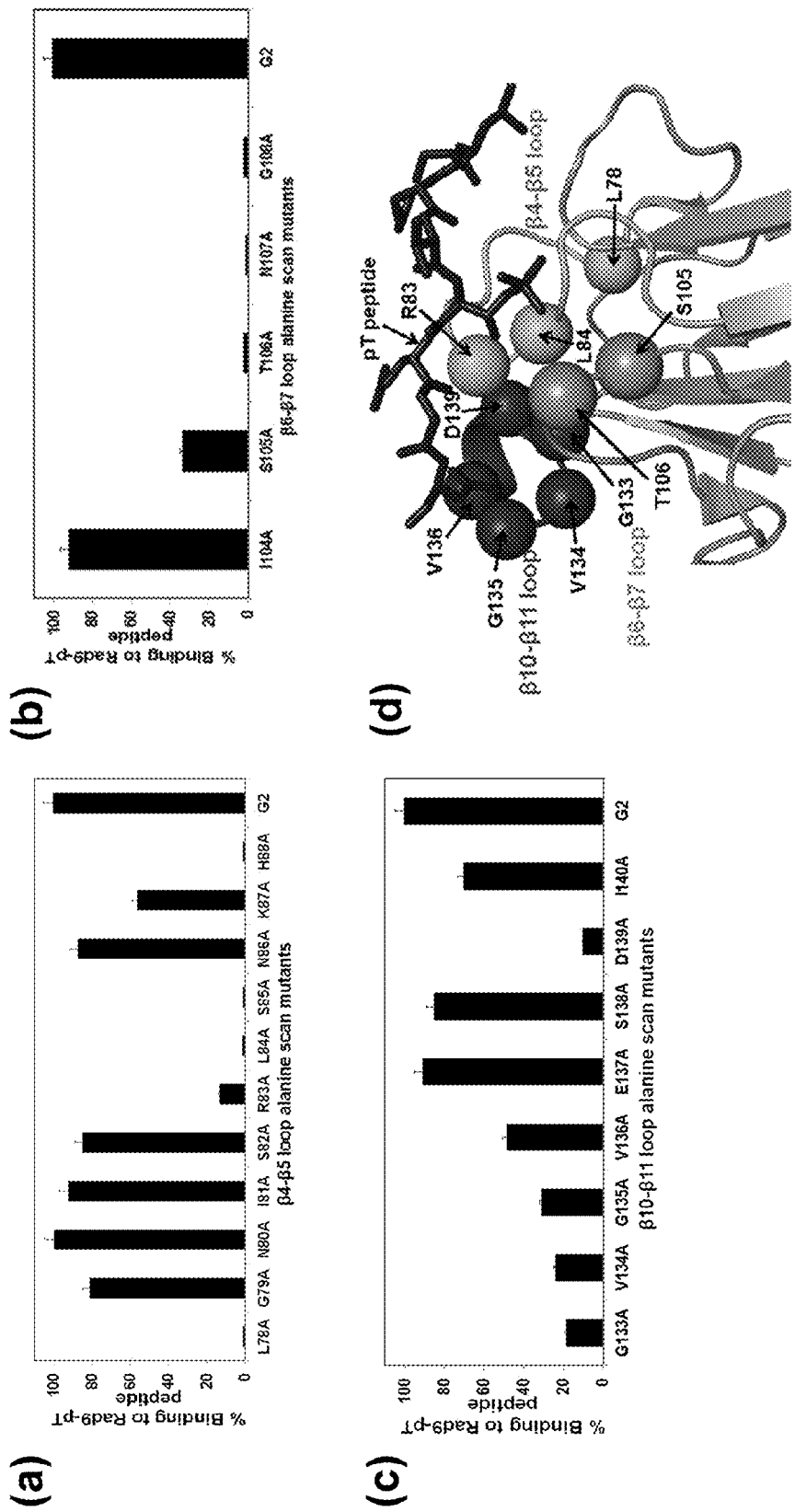
FIG. 13 shows the results of alanine-scanning experiments at amino acid residues from three loops in the FHA1 domain. Residues 78-88 in the β4-β5 loop, 104-108 in the β6-β7 loop, and 133-139 in the β10-β11 loop were mutated to alanine one at a time and the mutants were tested for binding to the Rad9-pT peptide by phage ELISA. Binding was detected using an anti-M13 antibody conjugated to HRP. Percent binding is shown by phage ELISA for β4-β5 loop alanine-scan mutants (FIG. 13(a)), β6-β7 loop alanine-scan mutants (FIG. 13(b)), and β10-β11 loop alanine-scan mutants (FIG. 13(c)). Binding of all the variants was normalized for the display of the Flag epitope. The binding signal of the G2 mutant for the Rad9-pT peptide was taken as 100% and the percentage binding of all the twenty-four alanine-scan mutants was calculated accordingly.
Figure 14:
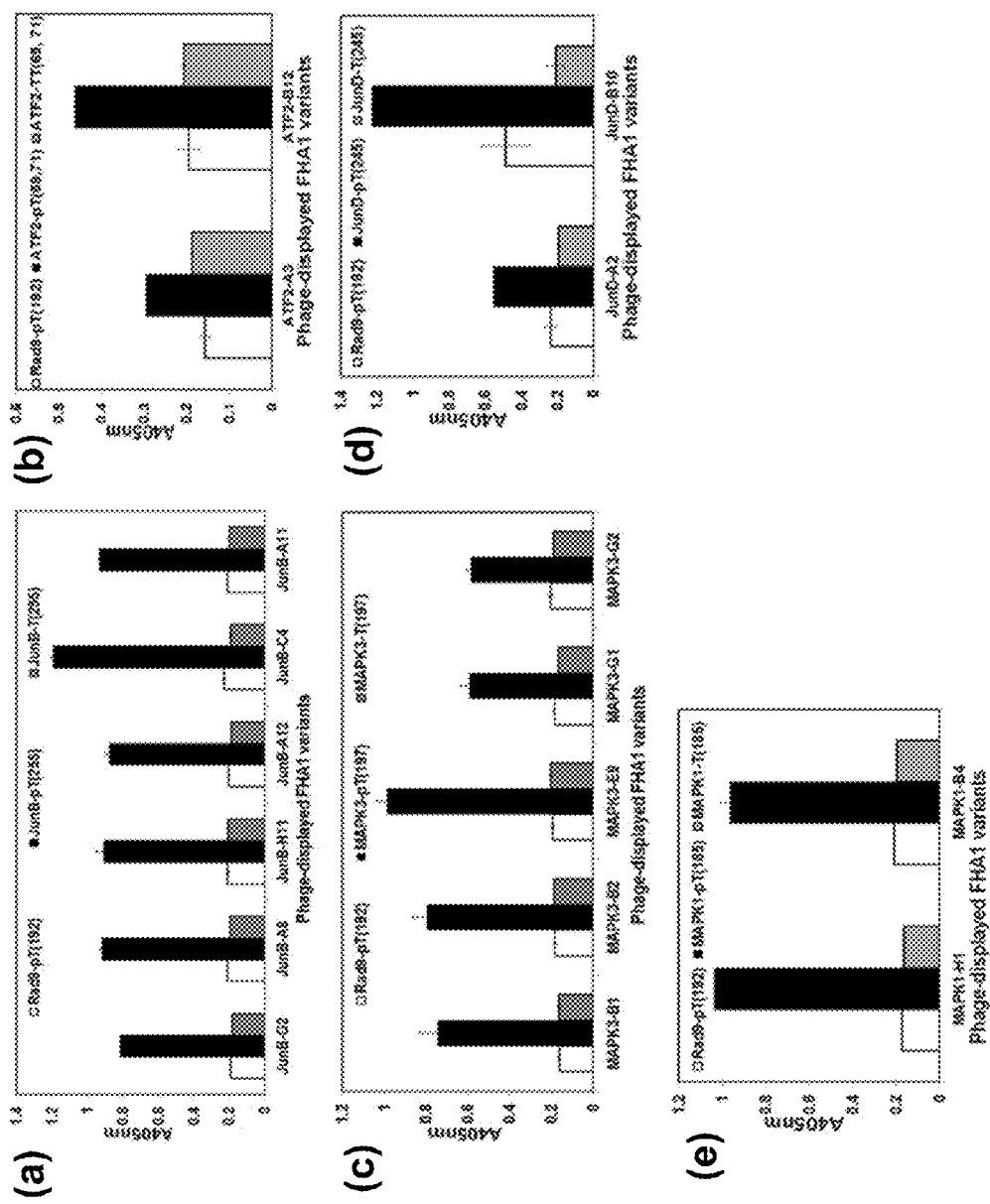
FIG. 14 are graphs of Rad-9-pT peptide binding of FHA1 variants with novel specificities. Phage-ELISA was performed after two rounds of affinity selection against five different pT-containing peptides. The peptides screened are from transcription factor jun-B, FIG. 14(a); activating transcription factor 2 (ATF2), FIG. 14(b); mitogen-activated protein kinase 3 (MAPK3), FIG. 14(c); transcription factor jun-D, FIG. 14(d); and mitogen-activated protein kinase 1 (MAPK1), FIG. 14(e). Binding to the cognate pT peptide (black histograms), the non-phosphorylated form of the same peptide (grey histograms) and the original pT peptide from yeast Rad9 protein (white histograms) are included in the five panels. Error bars represent standard deviation of duplicate measurements.
Figure 15:
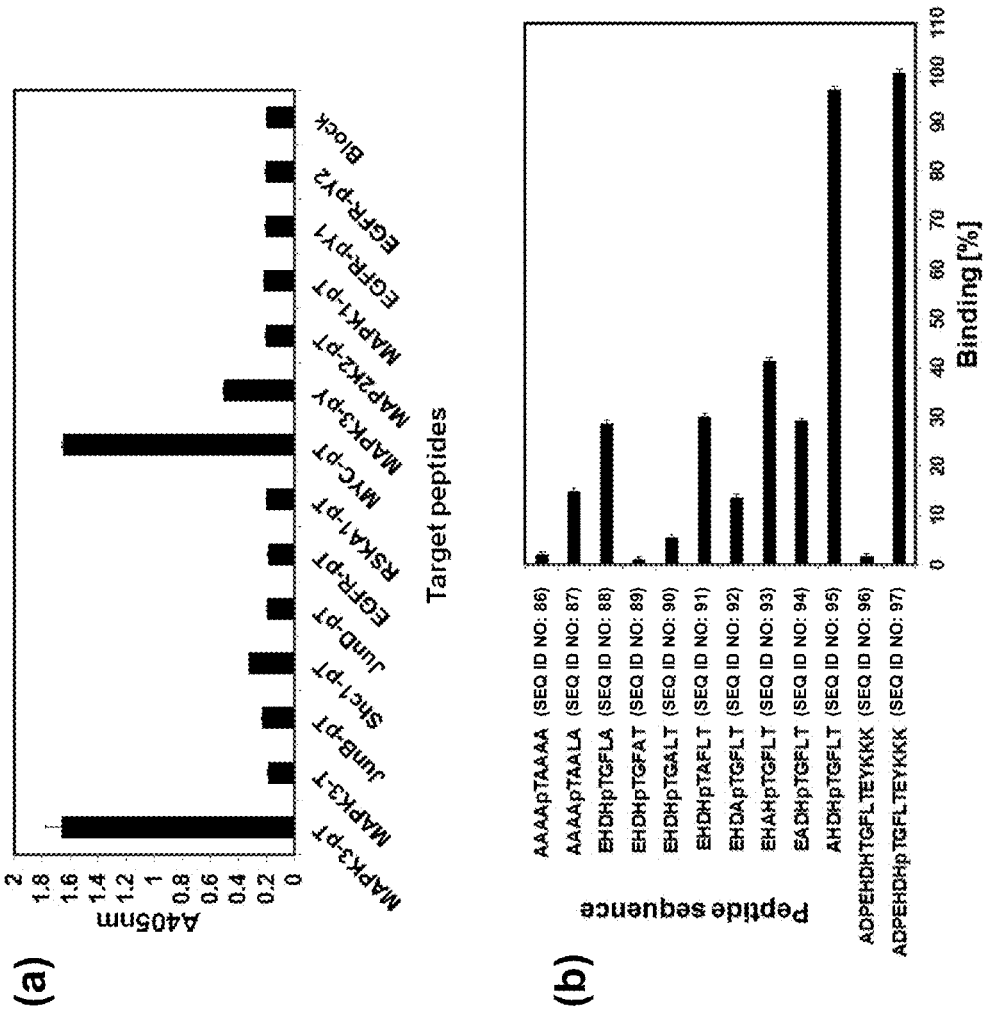
FIG. 15 show the results of experiments characterizing the specificity of an anti-MAPK3 affinity reagent, and determining the peptide residues important for interaction.
Figure 16:
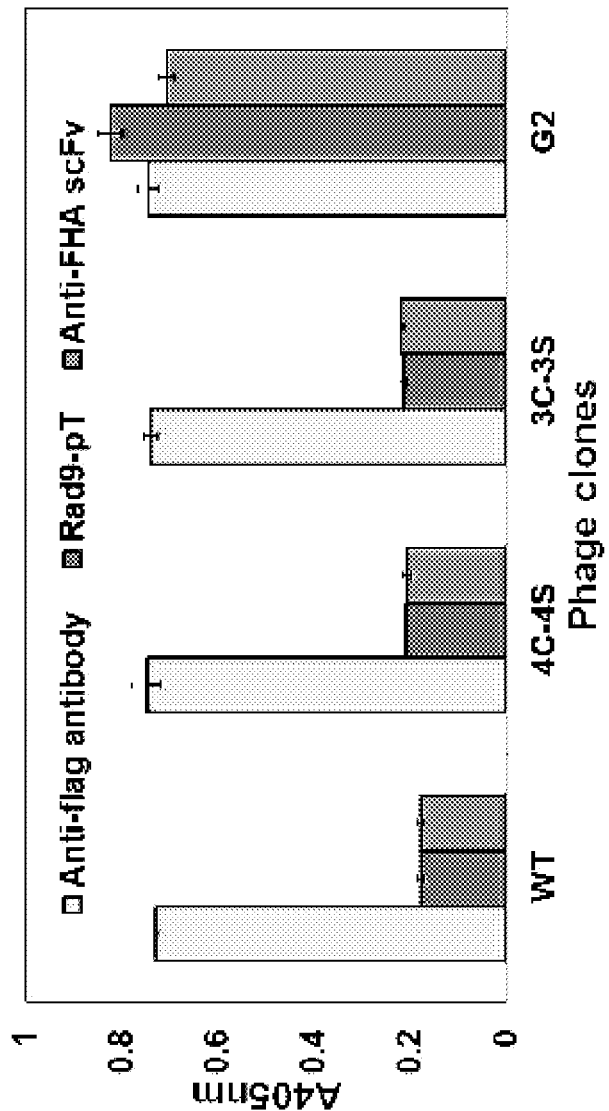
FIG. 16 is a bar graph showing folding of the phage-displayed WT FHA1 domain and its variants. As the phage-displayed WT FHA1 domain and its 3C-3S, 4C-4S, and D2 variants carry an N-terminal Flag epitope, ELISA values were normalized to the detection of the Flag epitope. Neither the phage-displayed WT FHA1 domain nor the 3C-3S and 4C-4S variants were recognized by the anti-FHA scFv, an antibody that recognizes a conformational epitope in the FHA1 domain. Only the D2 variant, which was selected for functional display (i.e., binding to the Rad9-pT peptide ligand), was recognized by the scFv. These results suggested that among the four tested FHA1 domains, only the D2 variant was properly folded when fused to protein III of bacteriophage M13.
Figure 21:
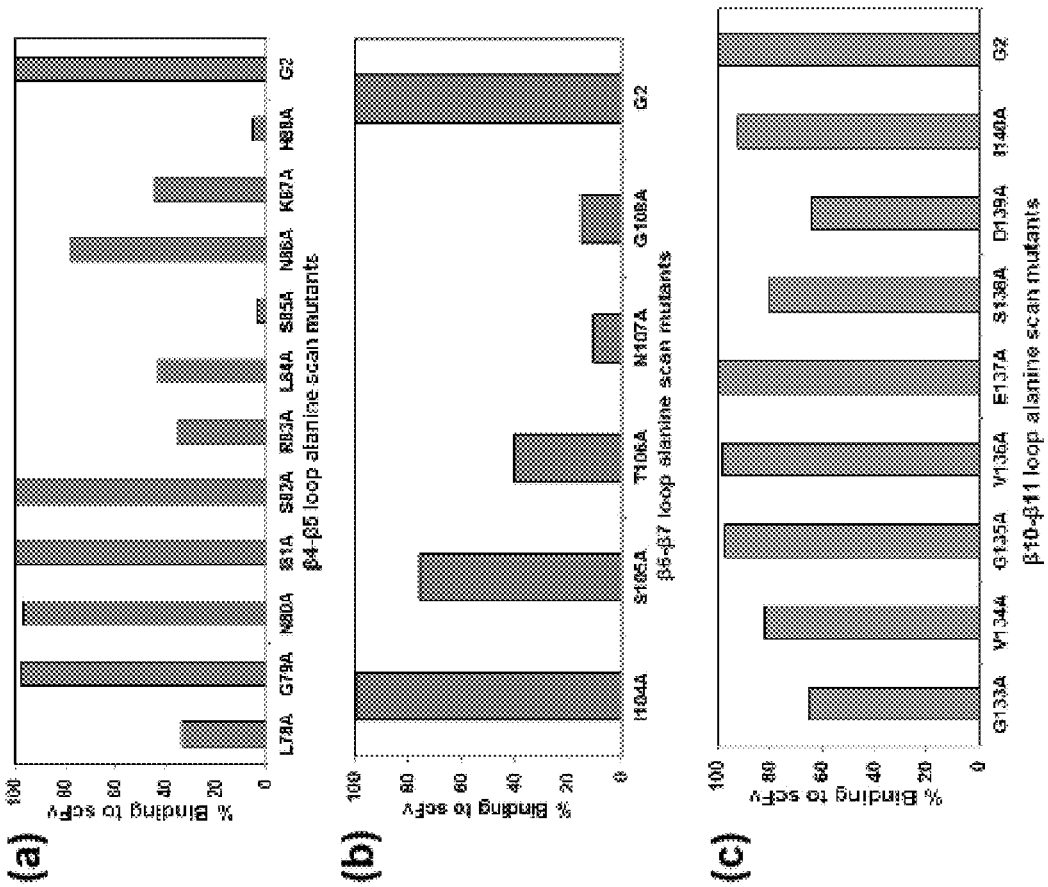
FIG. 21 are bar graphs showing detection of folded alanine-scan mutants. Phage-displayed alanine-scan point mutants were tested for binding to an antibody fragment that recognizes only folded FHA 1 variants.

Alanine-Scanning to Determine the FHA1 Residues Important for Interaction with the pT Peptide To determine which residues in the G2 variant are important for interaction with the pT peptide (SLEVpTEADATFY-AKK) (SEQ ID NO:9), alanine-scanning of each of the residues from the three loops (11 from β4-β5, 5 from β6-β7, and 8 from β10-β11) was performed and binding of the mutants to the cognate pT peptide was tested by phage ELISA (FIG. 13a-c). Five mutants (L78A, R83A, L84A, S85A, and H88A) from the β4-β5 loop, four mutants (S105A, T106A, N107A, and G108A) from the β6-β7 loop, and five mutants (G133A, V134A, G135A, V136A, and D139A) from the β10-β11 loop had reduced or no binding to the pT peptide when mutated to alanine, indicating that the interaction of these residues with the pT peptide is important for binding. Four out of these 14 mutations (S85A, H88A, N107A, and G108A) destroyed folding or denatured the FHA1 domain as determined by using a recombinant antibody that recognized folded, but not denatured, FHA1 domain (FIG. 21). Therefore, 10 residues from the three loops, 3 from β4-β5 (green spheres), 5 from β10-β11 (red spheres), and 2 from β6-β7 (orange spheres) were identified to be critical for pT peptide recognition (FIG. 13d) and not for folding of the FHA1 domain. These residues are good candidates for oligonucleotide-directed mutagenesis to generate a phage-displayed library of FHA1 variants that can be screened against various pT peptides. According to our alanine-scanning experiments, the G133A and G135A mutants showed reduced binding to the pT peptide (SLEVp-TEADATFYAKK) (SEQ ID NO:9), indicating that these two positions in the FHA1 domain play an important role in interaction with the pT peptide, as previously described (Yongkiettrakul et al. (2004) *Biochemistry* 43, 3862-9).

Example 11

Fluorescence-Based Thermal Shift (FTS) Assay

The FTS assay was performed on a MxPro-Mx3005P instrument (Stratagene) following the protocol described by Giuliani et al (Giuliani et al. (2008) *Biochemistry* 47, 13974-84). It is a real-time assay using the SYBR® Green experiment setting with dissociation curve. The default FRROX filter set was used with an excitation wavelength of 492 nm and emission wavelength of 610 nm. FHA1 domains diluted with PBS to 2× final concentration (i.e. 2 µM and 8 µM) were mixed with 10×SYPRO® Orange protein gel stain (Invitrogen; 5000× concentration in DMSO) to give a final dye concentration of 10×. Then, to the protein wells only, 10 µL of the dye+protein mixture was added along with 10 µL of 1×PBS buffer. In other wells, 10 µL of either the pT peptide or its non-phosphorylated form (diluted to 2× final concentration with PBS, i.e. 100 µM and 500 µM) was added to 10 µL of dye+protein mixture. The final reaction volume was 20 µL with final concentrations of 1 µM or 4 µM of FHA1 domains, 50 µM or 250 µM of pT and non-phosphorylated peptides and 5× final concentration of the SYPRO® Orange. The assay was performed in duplicate in 96 well white PCR plates (BIO-Rad) covered with optically clear Microseal® 'B' Film (Bio-Rad) and heated from 25° C. to 95° C. and the melting curve was obtained with fluorescence (R) values plotted on the Y-axis and increasing temperature (° C.) on the X-axis. The mid-point of the curve gives the melting temperature ($T_m$), which shifts to a higher temperature in the presence of the pT peptide.

Example 12

Thermal Stability of the D2 Variant and Selection of More Stable Variants

Figure 8:
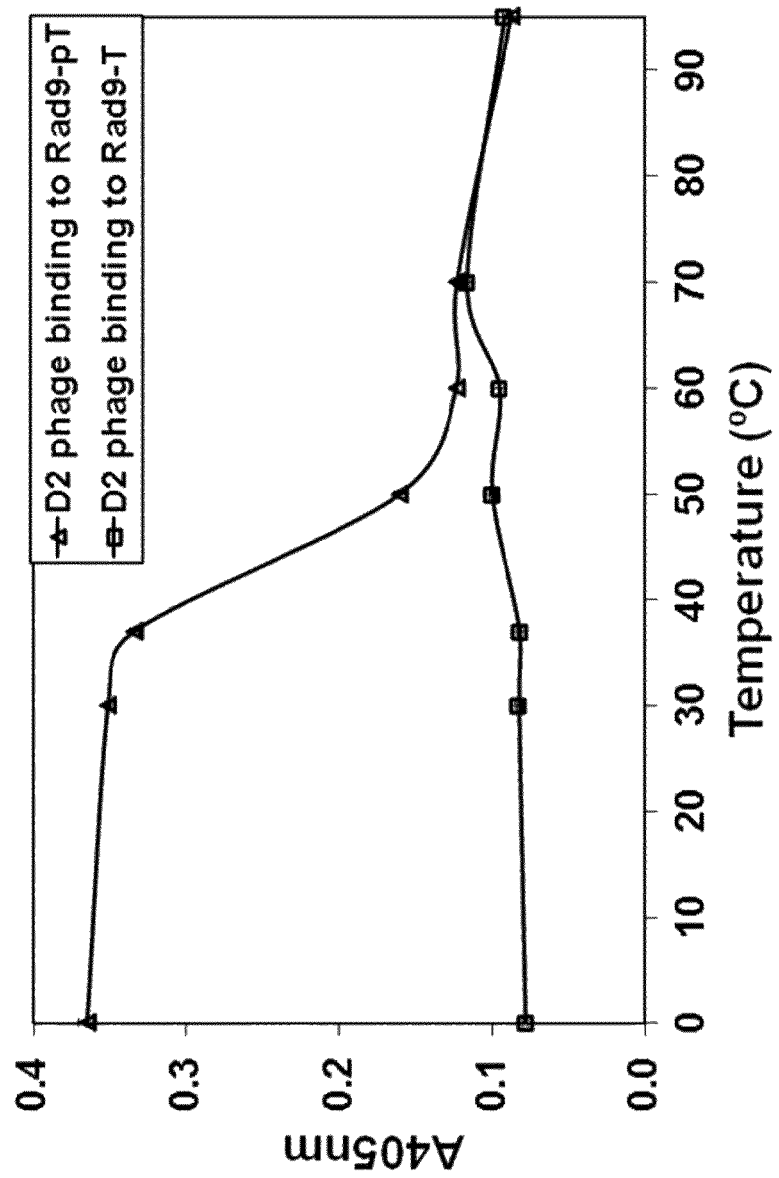
FIG. 8 is a graph showing thermal stability of bacteriophage particles displaying the D2 variant. Phage particles displaying the D2 variant were heated at various temperatures (30° C., 37° C., 50° C., 60° C., 70° C., 80° C. and 95° C.) for 3 h and allowed to cool to room temperature. The treated phage particles were then incubated with the cognate pT peptide (Rad-pT; squares) and the negative control peptide (Rad9-T; circles) immobilized on plastic via neutravidin. Phage binding was detected using an anti-M13 antibody conjugated to HRP.

To evaluate the thermal stability of the D2 variant, phage particles displaying the D2 variant were heated at various temperatures (30° C., 37° C., 50° C., 60° C., 70° C., 80° C., and 95° C.) prior to incubation with the cognate pT peptide (Rad9-pT) and the non-phosphorylated form of the same peptide (Rad9-T). Phage ELISA showed that the D2 variant was functional when heated at 30° C. and 37° C., but there was a drastic drop in binding (~60%) upon heating above 50° C. (FIG. 8). The D2 variant (purified six-his tagged protein) was mixed with SYPRO orange dye with or without the Rad9-pT-containing peptide and heated from 25° C. to 95° C. in a real-time PCR experiment known as the Fluorescence-based thermal shift (FTS) assay[36]. In this assay, initially, the fluorescence of SYPRO orange dye is quenched in the aqueous environment of a folded protein, but as the protein starts to unfold upon heating, the dye interacts with the hydrophobic core of the protein and its fluorescence increases. Therefore, an increase in fluorescence of the dye is directly proportional to protein unfolding, until a temperature (referred to as $T_m$ here) is reached at which the dye fluorescence decreases due to aggregation and precipitation of the protein. The melting temperature ($T_m$) of the D2 variant was determined by fluorescence-based thermal shift (FTS) assay to be approximately 5° C. lower than the $T_m$ of the WT FHA1 domain. To improve the thermal stability of the D2 variant, affinity selection was carried out by heating the phage library displaying D2 variants at 50° C. prior to incubation with the pT peptide ligand to favor the isolation of variants that remained folded and functional above 50° C.

Example 13

Improved Thermal Stability, Expression and Affinity of a Recombinant Antibody Fragment To improve the thermal stability, expression and affinity of a recombinant antibody fragments, a mutagenic library (6.5× $10^7$ variants) was constructed using the D2 coding sequence as the starting template by following the protocol for mutagenic PCR (Cadwell et al. (1994) *PCR Methods Appl* 3, S136-40). Random mutations were generated in the coding region of the D2 variant. The expected number of mutations is the same as described for the 3C-3S mutagenic library. Sequencing 60 library members revealed that the D2 library contains ~8% wild type, 16%, 20%, 23%, 15%, and 10%, with 1 to 5 mutations, respectively, and 8% had 6 or more mutations. Three rounds of affinity selection with the phage library, which was heated to 50° C., yielded five FHA1 variants (A12, H7, G7, A1 and G2) that were more thermally stable than the starting D2 domain. The mutations observed in each one of the thermally stable mutants are listed in Table S2.

TABLE S2

Mutations observed in the thermally stable FHA1 domain variants.

| FHA1 domain variant[a] | No. of mutations | Mutations | Location[b] |
|---|---|---|---|
| A1 | 2 | N121Y | β8-β9 loop |
|  |  | L141I | β11 strand |
| G2 | 3 | T15A | N-terminus |
|  |  | L48F | β2 strand |
|  |  | N121Y | β8-β9 loop |
| H7 | 5 | Q16R | N-terminus |
|  |  | T39P | β1-β2 loop |
|  |  | K59E | β2-β3 loop |
|  |  | C74S | β3-β4 loop |
|  |  | G94D | β5-β6 loop |
| G7 | 5 | S11T | N-terminus |
|  |  | A14V | N-terminus |
|  |  | S82R | β4-β5 loop |
|  |  | N121Y | β8-β9 loop |
|  |  | L141I | β11 strand |
| A12 | 4 | C74S | β3-β4 loop |
|  |  | G94D | β5-β6 loop |
|  |  | E129V | β10 strand |
|  |  | N158I | C-terminus |

[a]FHA1 variants that are thermally more stable than the starting D2 variant.
[b]β = beta-strand. Loop is the region between two β-strands. The N-terminal mutation is present before the β1-strand and C-terminal mutation is after the β11-strand.

Mutations were observed in 4 out of 11 β-strands, and in 4 loops of which two loops β3-β4 and β4-β5 are involved in interaction with the pT peptide ligand and the other two loops β1-β2 and β8-β9 do not interact with the pT peptide ligand. Several mutations were also observed at the N-terminus of the FHA domain, before the β1-strand, indicating that this region may be critical for structural and thermal stability.

Figure 11:
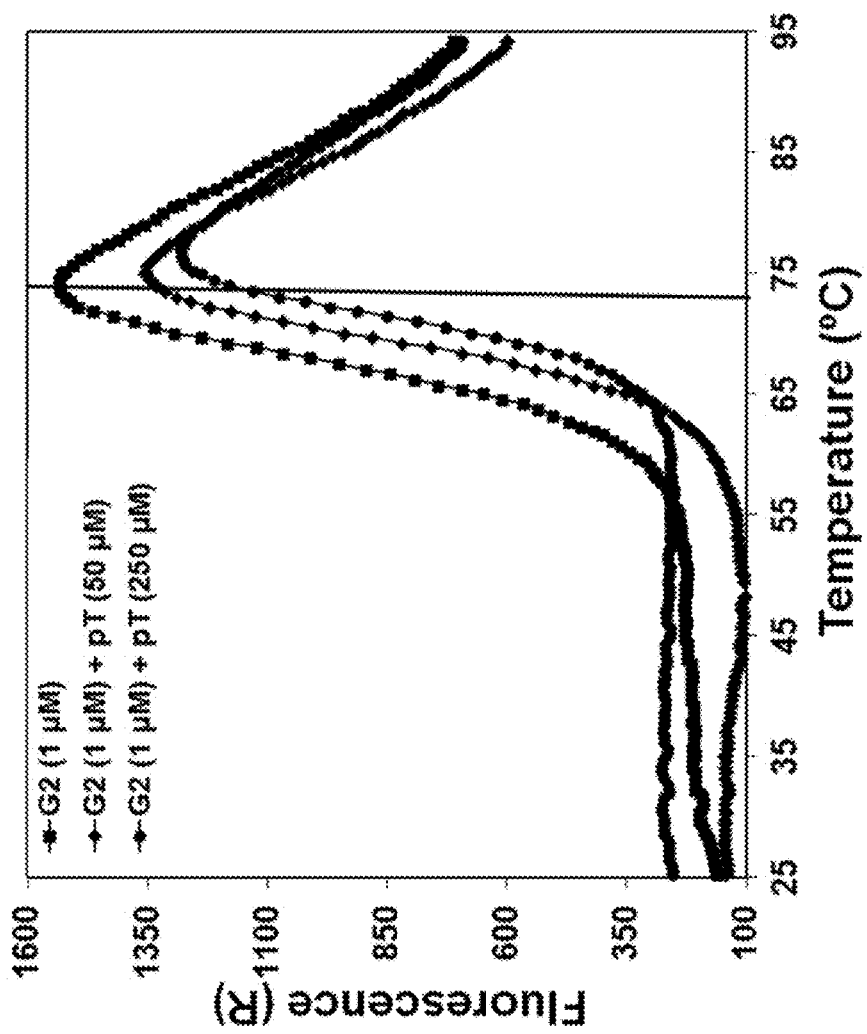
FIG. 11 is a graph showing a determination of the $T_m$ of FHA1 variants by FTS Assay. The FHA1 domain variant was mixed with SYPRO orange dye, and heated from 25° C. to 95° C. on an Mx3000P Real-time thermal cycler instrument. When the protein domain was in its native conformation, the SYPRO orange dye signal was quenched in the aqueous environment, but when the dye interacts with the protein domain undergoing thermal denaturation, its fluorescence increased upon exposure to the protein's hydrophobic core (Bridges et al. (2005) Sci STKE 2005, re10). The melting curve for the G2 variant (without any peptide) is shown as boxes. The shift in $T_m$ in the presence of 50 μM and 250 μM of the pT peptide are shown as diamonds and circles, respectively.

The $T_m$ values of FHA1 variants were determined by FTS assay (Giuliani et al. (2008) *Biochemistry* 47, 13974-84). A representative $T_m$ curve for the G2 variant at 1 µM concentration is shown (solid squares), alone and in the presence of the pT peptide (FIG. 11). No shift in the $T_m$ was observed in the presence of the non-phosphorylated form of the same peptide (data not shown). The $T_m$ values of the thermally stable variants (along with WT and D2 variant) at 1 µM and 4 µM concentration, along with the $T_m$ shift in the presence of two different concentrations (50 µM and 250 µM) of the pT peptide, are listed in Table S3.

TABLE S3

The $T_m$ values for various FHA1 domain variants along with the $T_m$ shifts in the presence of the cognate pT peptide.

| FHA domains | Protein concentration (µM) | $T_m$ (° C.)[a] | $T_m$ shift (° C.) in the presence of pT peptide[b] | |
|---|---|---|---|---|
|  |  |  | 50 µM | 250 µM |
| WT | 1 | 66.7 | 1.7 | 3.8 |
|  | 4 | 66.4 | 1.95 | 3.55 |
| D2 | 1 | 61.6 | 2.6 | 4.6 |
|  | 4 | 61.8 | 1.85 | 4.45 |
| A12 | 1 | 66 | 1.25 | 2 |
|  | 4 | 64 | 1 | 2.4 |
| H7 | 1 | 65.2 | 1.25 | 3 |
|  | 4 | 65.1 | 1.35 | 3.65 |
| G7 | 1 | 67 | 4 | 6.5 |
|  | 4 | 65.7 | 3.5 | 6.3 |
| A1 | 1 | 68.5 | 1.2 | 3.95 |
|  | 4 | 68.8 | 1.2 | 4.5 |

TABLE S3-continued

The $T_m$ values for various FHA1 domain variants along with the $T_m$ shifts in the presence of the cognate pT peptide.

| FHA domains | Protein concentration (μM) | $T_m$ (° C.)[a] | $T_m$ shift (° C.) in the presence of pT peptide[b] 50 μM | 250 μM |
|---|---|---|---|---|
| G2 | 1 | 73.75 | 1.2 | 2.75 |
|  | 4 | 74.9 | 0.5 | 2.5 |

[a]The temperature corresponding to the mid-point of the melting curve/thermal denaturation curve is the melting temperature ($T_m$).
[b]An increase in $T_m$ is observed when the FHA1 variants are incubated with the pT peptide and heated from 25° C. to 95° C. The $T_m$ shift corresponds to this increase in $T_m$ value.

Therefore, using high temperature during affinity selection enabled the isolation of variants with favorable mutations that improved the thermal stability as well as their protein expression in *Escherichia coli*. The yields per liter of bacterial culture for the thermally stable variants, A12, H7, G7, A1 and G2 are 36, 37, 43, 56, and 63 mg, respectively.

Example 14

Determining the Dissociation Equilibrium Constants ($K_d$) by Isothermal Calorimetry (ITC)

Figure 12:
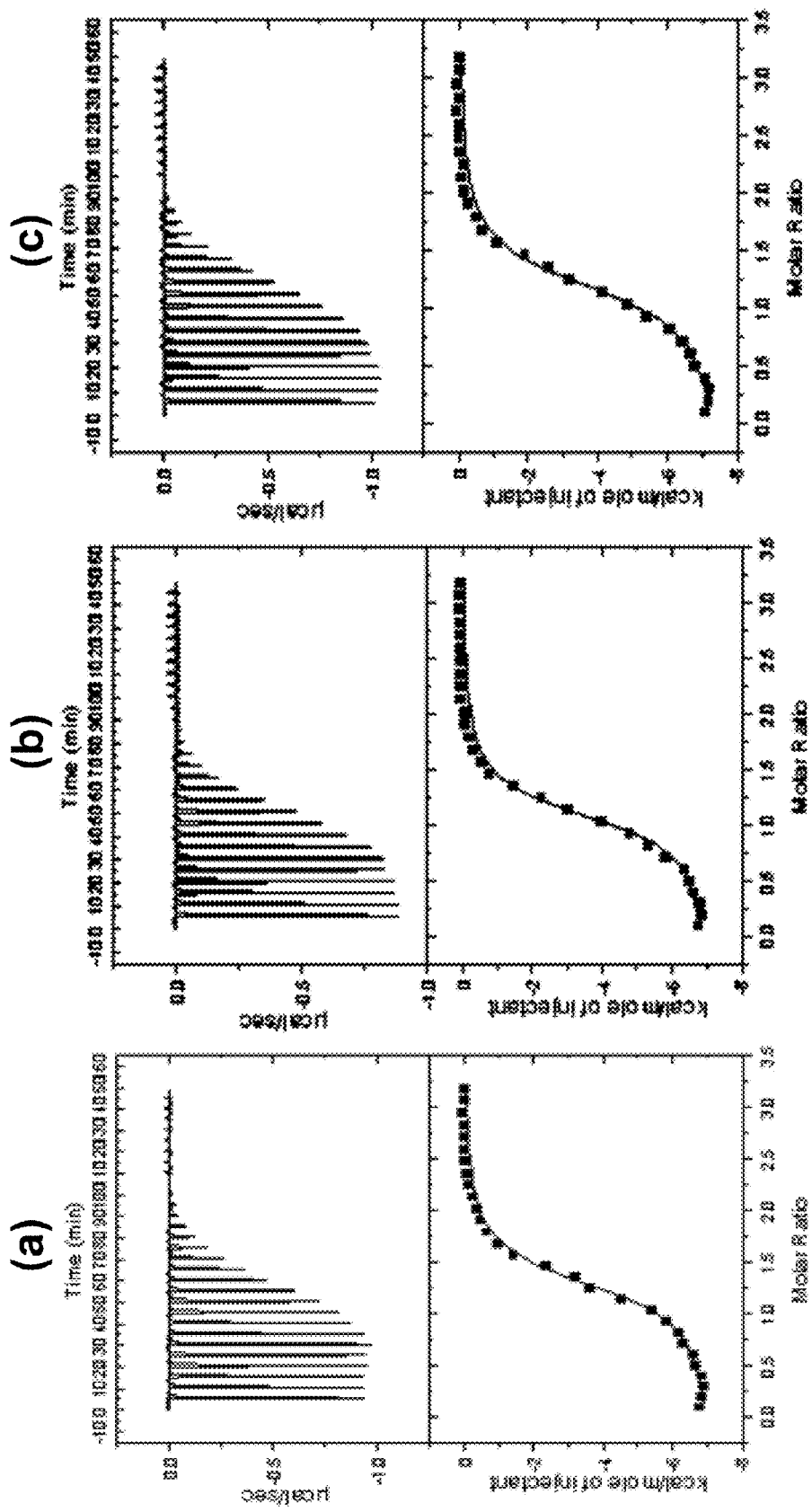
FIG. 12 shows the results of experiments to determine the $K_d$ in solution by ITC. A fixed amount (10 μL) of the pT peptide (Rad 9-pT: SLEVpTEADATFYAKK (SEQ ID NO:9); 500 μM) was injected from the syringe into the sample cell containing the FHA1 domain (35 μM). The $K_d$ values of the WT FHA1 domain (FIG. 12 (a)), D2 variant (FIG. 12(b)) and G2 variant (FIG. 12(c)), were determined to be 1±0.17 μM, 0.97±0.15 μM and 0.89±0.1 μM, respectively. A stoichiometry of 1:1 was observed for all the three FHA1 domains with their pT peptide complexes. Each measurement was repeated three times.

The affinity of the G2 variant and the WT FHA1 domain to the pT peptide (SLEVpTEADATFYAKK) (SEQ ID NO:9) was determined by ITC (FIG. 12). The sample cell contained the purified FHA1 domains (35 μM) and the injection syringe was filled with the pT peptide (350 μM). As seen in FIG. 12, the G2 variant bound with a $K_d$ of ~0.89 μM, which was similar to the $K_d$ (~1 μM) of WT FHA1 domain. The FHA1 domains bound to the pT peptide with a stoichiometry of 1:1, and the ITC graph was fitted by the single site binding model. The ITC results revealed that the thermally stable G2 variant and the WT FHA1 domain bound to the pT peptide with similar affinities. The previously reported $K_d$ for WT FHA1 domain by ITC is 0.53 μM (Durocher et al. (2000) *Mol Cell* 6, 1169-82).

Example 15

Figure 2:
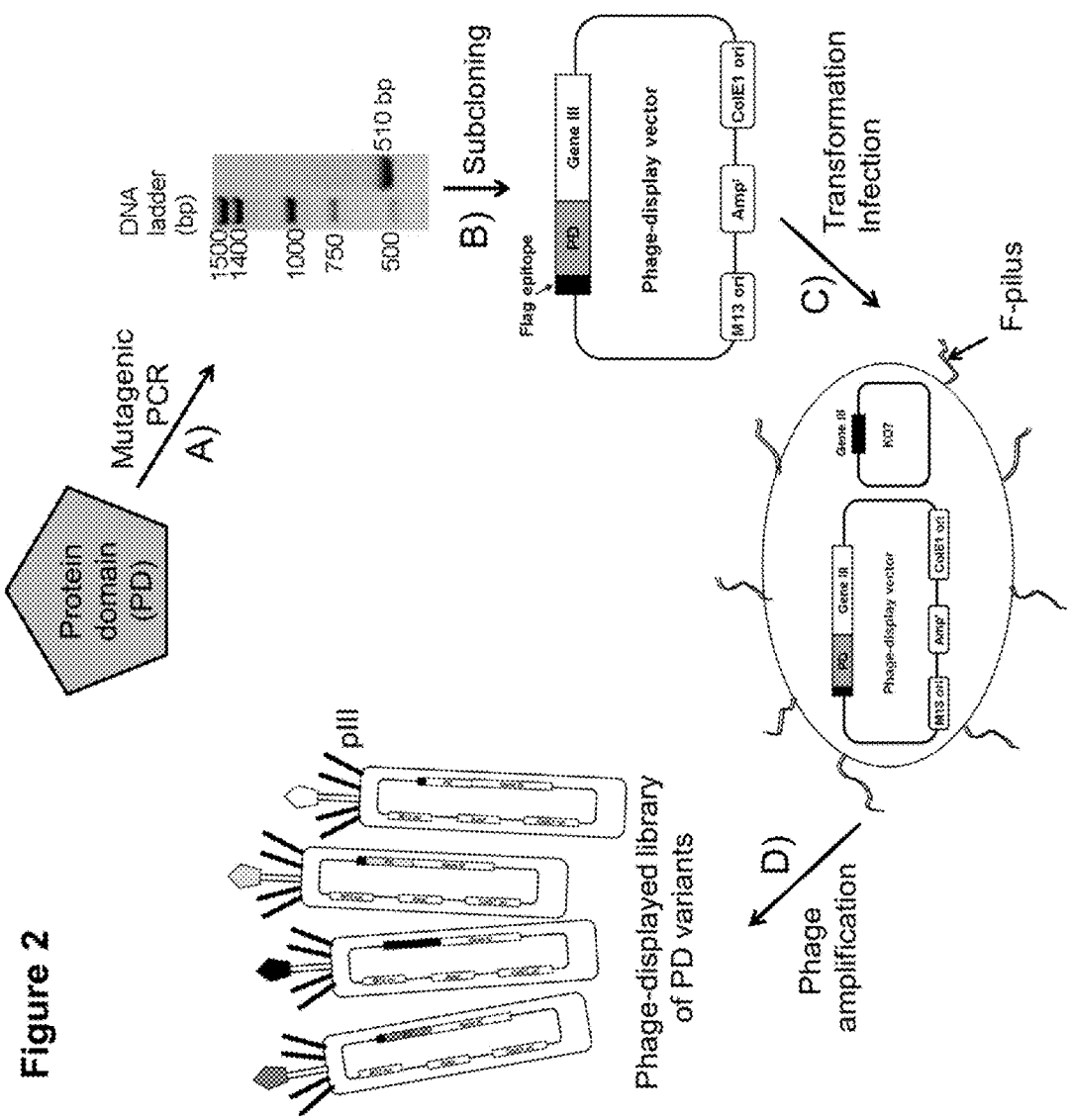
FIG. 2 is a diagrammatic representation of a scheme for constructing a phage-displayed library of the protein domain variants.

Isolating and Evaluating Thermally Stable Affinity Reagents and Constructive a Phage-Displayed Library of Protein Domain Variants A phosphopeptide-binding domain was found to be non-functional when displayed on the surface of bacteriophage M13 as a protein III (pIII) fusion. While we were able to identify a functional variant of this domain through mutagenesis (unpublished data), we observed it to be thermally less stable than the wild-type form of the domain. Therefore, we decided to use mutagenic polymerase chain reaction (PCR) to construct a library of variants and isolate thermally stable variants from it, which still retained binding to the target peptide, when displayed on the phage surface. For this purpose, the coding sequence of the protein domain (PD) variant was amplified by error prone PCR (Cadwell et al. (1994) *PCR Methods Appl* 3, 136-40). The PCR product, containing the insert pool, was purified using QIAquick@ PCR purification kit (Qiagen), resolved by 1% agarose gel electrophoresis, and confirmed to be of the correct size (FIG. 2A). The insert pool was subcloned into a modified version of the pAPIII$_6$ phage-display vector (Haidaris et al. (2001) *J Immunol Methods* 257, 185-202), with an 8 amino acid long FLAG epitope (Brizzard et al. (2001) *Curr Protoc Neurosci Ch.* 5, Unit 5.8) at the N-terminus and in-frame with the gene III coding sequence at the C-terminus (FIG. 2B). TG1 electrocompetent cells were transformed with the library DNA and the cells were plated on LB/CB plates (Luria Bertani broth: 1% tryptone, 0.5% yeast extract, 1% sodium chloride; with 50 μg/mL carbenicillin). The library diversity was $6.5 \times 10^7$. In order to determine the error rate of mutagenic PCR, 60 clones were sequenced, of which 8% were wild type, and 16%, 20%, 23%, 15%, 10%, 2%, 5%, 2% clones had one through eight mutations, respectively. To allow phage propagation, the cells harboring the library DNA Were grown to mid-log (00600=0.5-0.6) and infected with the helper phage M13 K07 (multiplicity of infection of 20; FIG. 2C). Phage amplification was carried out overnight at 30° C. (FIG. 2D), the library of phage particles, displaying the protein domain variants, was purified using a mixture of 24% polyethylene glycol/3 M NaCl and aliquots were stored at −80° C.

Example 16

Determining the Appropriate Temperature for Affinity Selection

Figure 6:
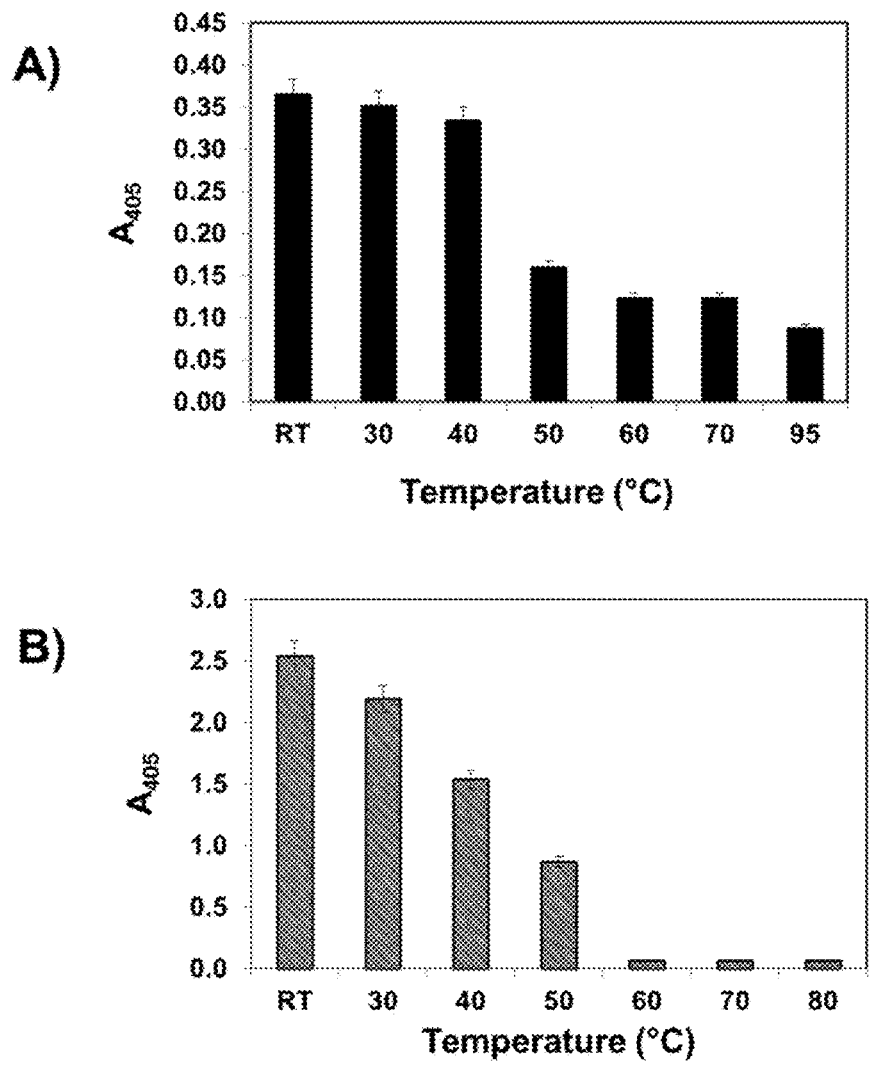
FIG. 6 are graphs showing a determination of selection pressure temperature.

In order to isolate variants that are more thermally stable than the starting domain, it is important to determine the thermal stability profile of the domain. Phage particles displaying the starting domain were either incubated at room temperature (RT) or heated at various, elevated temperatures (30° C., 40° C., 50° C., 60° C., 70° C., and 95° C.) for 3 hr and allowed to cool to RT. The biotinylated phosphopeptide (500 ng/well) was immobilized on Nunc™ microtiter plate (Fischer Scientific) wells via NeutrAvidin (Thermo Scientific; 1 μg/well), and blocked with 2% skim milk in ix PBS. The treated phage particles were incubated with the target phosphopeptide ($5 \times 10^{10}$ phage/well) and the binding phage were detected using anti-M13 antibody conjugated to Horseradish Peroxidase (HRP; GE Healthcare) (FIG. 6A). Similar heat treatment was performed using the purified protein domain (5 μg/well; purified by immobilized metal affinity chromatography using Ni-NTA agarose (Qiagen) via the C-terminal hexahistidine tag) and binding was detected using anti-His antibody conjugated to HRP (Sigma-Aldrich; FIG. 6B). It was observed that when the domain was heated at 50° C., there was a 60% drop in binding, compared to the binding of the domain that had not been heated. Thus, the hypothesis is that performing selections at this temperature will eliminate variants that are less stable than 50° C. This effort is based on prior efforts demonstrating that the thermal stability, expression and affinity of a single-chain Fragment of variable region (scFv) could be improved using a chain shuffled library and employing high temperature and denaturants during affinity selection (Jung et al. (1999) *J Mol Biol* 294, 163-180. We have extended this approach to a phosphopeptide-binding domain using mutagenic PCR to construct the library and high temperature as selective pressure during biopanning.

Example 17

Affinity Selection for Isolating Thermally Stable Protein Domain Variants

Figure 3:
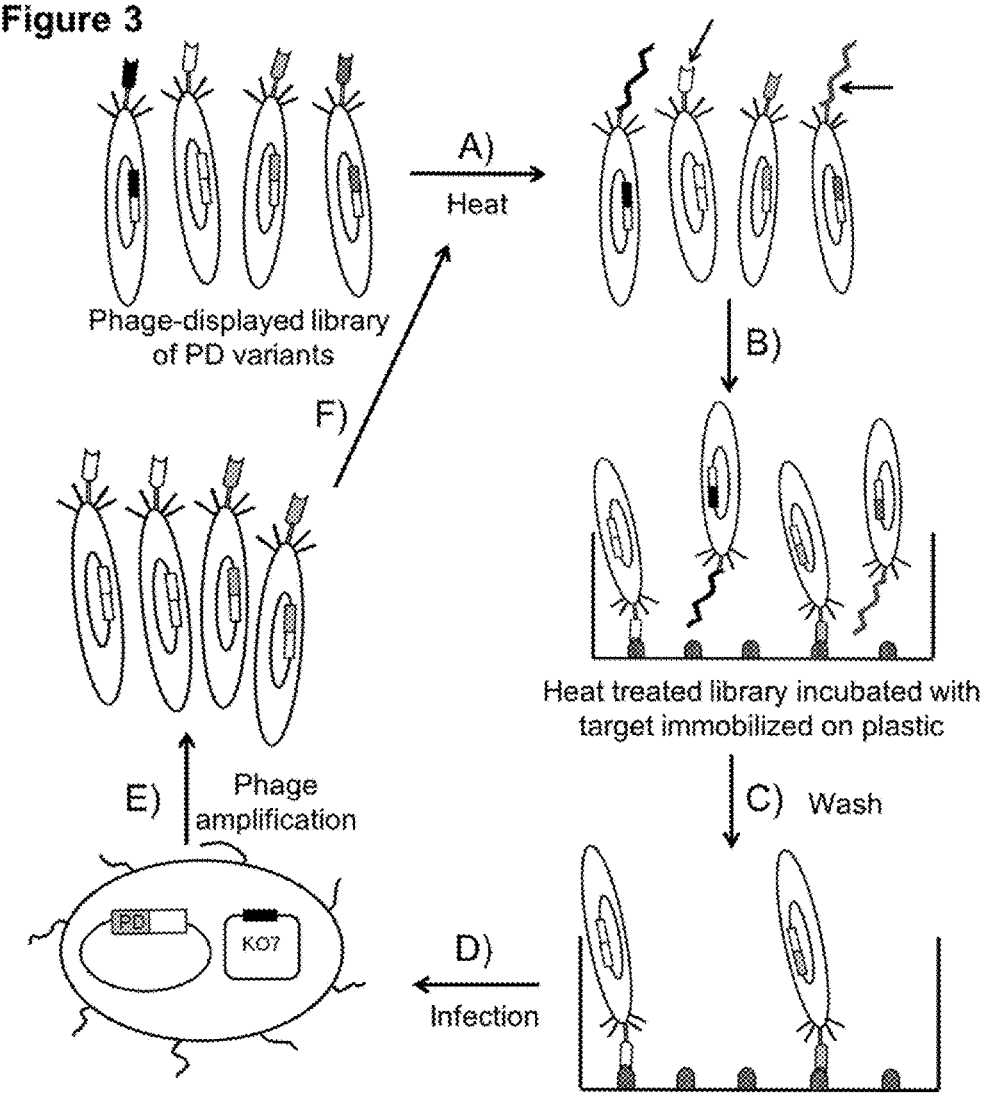
FIG. 3 is a schematic representation of the affinity selection process.
Figure 4:
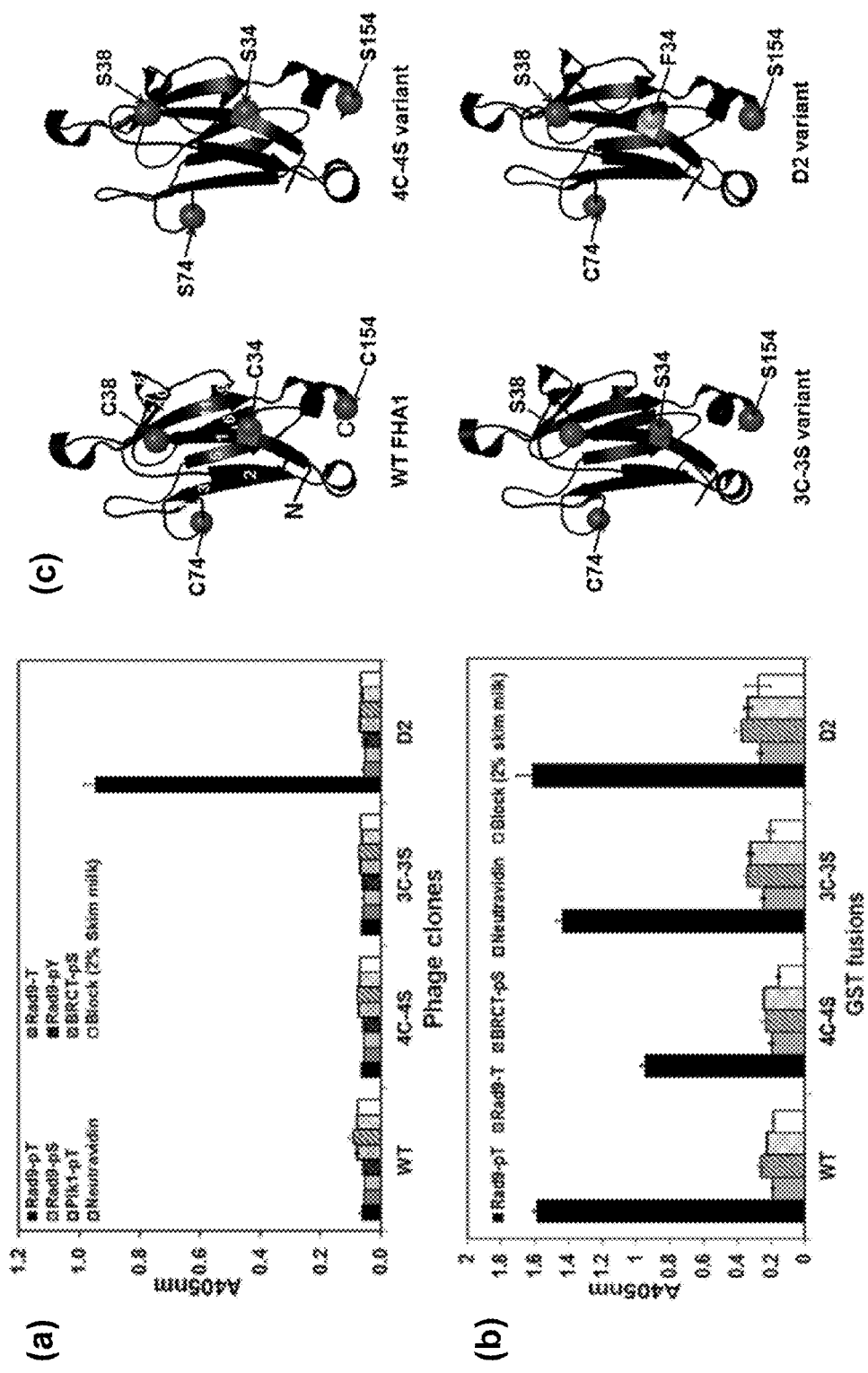
FIG. 4 shows graphs (FIGS. 4A and 4B) and a diagram (FIG. 4C) illustrating the results of enzyme-linked immunosorbent assays (ELISA) for detecting interaction between the FHA1 domain and the immobilized pT peptide ligand.

In another embodiment, three rounds of affinity selection were performed applying high temperature as the selective pressure to eliminate thermally unstable variants of the protein domain. During the first round of selection, the phage library was pre-heated before the selection process at 40° C. for 3 hr and cooled to RT (FIG. 3A) to denature and inactivate variants that are unstable at this temperature. The treated phage library (150 µL) was incubated with the peptide ligand (2 µg) immobilized on Nunc™ MaxiSorp polystyrene tube (Fisher Scientific) via NeutrAvidin (2 µg; Thermo Scientific) and blocked with 2% skim milk in 1×PBS (FIG. 3B). After washing away the unbound/non-specific phage particles (FIG. 3C), the binding phage were eluted with 150 µL of 100 mM glycine-HCl (pH 2), and neutralized using 9 µL of 2 M Tris-base (pH 10). Eight hundred µL of TG1 *E. coli* cells (genotype: supE thi-1 D(lac-proAB) hsdD5[F' traD36 proAB+laclq lacZDM15]) at mid-log ($OD_{600nm}$=0.5-0.6) were infected with the entire volume of the eluted phage for 40 minutes at 37° C. and the cells were plated on an LB/CB plate and incubated overnight at 30° C. The cells, harboring the genomes of phage particles recovered from round one, were grown to mid-log ($OD_{600nm}$=0.5-0.6) and infected with M13 KO7 helper phage (MOI=20; New England BioLabs) (FIG. 3D) for phage propagation. Phage particles were amplified overnight at 30° C. and the enriched phage library (FIG. 3E) was purified by precipitation with 24% polyethylene glycol, 3 M NaCl, and carried forward for the second round of selection (FIG. 3F). The next two rounds of affinity selection was more stringent by heating the phage library at 50° C. for 3 hr, and cooling it to RT, before incubating with the peptide ligand. The experimental procedure for rounds #2 and #3 is the same as round #1, except that the volume of eluted phage used to infect TG1 cells is decrease with each subsequent round (i.e., half and one quarter of the total eluted phage was used for infection in rounds #2 and #3, respectively). After the third round of selection, there should be enrichment of variants that are thermally more stable than the starting clone, if they existed in the mutagenized library.

Example 18

Effect of High Temperature on Eliminating Thermally Less Stable Clones

Figure 7:
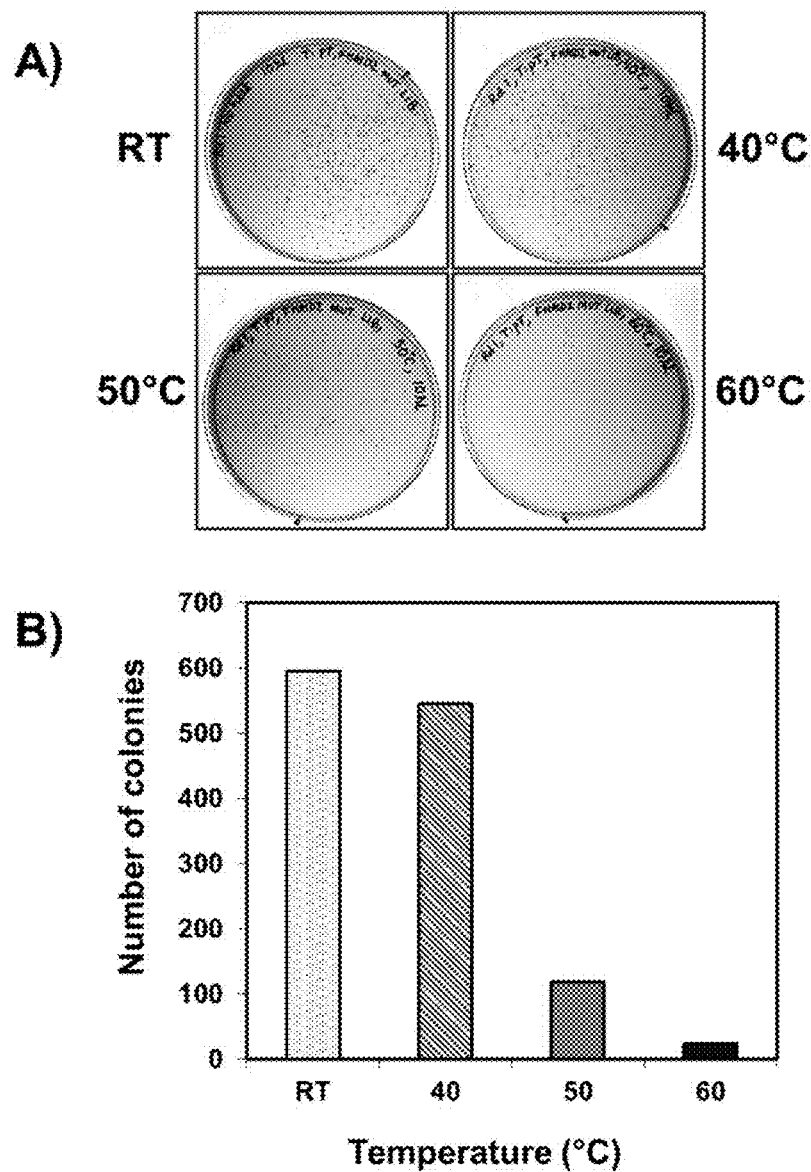
FIG. 7 shows experimental results establishing that elevated temperature works as a selective agent.

In order to confirm that elevated temperatures were effective in eliminating thermally unstable phage clones, the phage library was heated at 25° C., 40° C., 50° C. or 60° C. for 3 hr, followed by cooling to room temperature. Round #1 selection was performed against the target peptide using both the heat-treated and untreated libraries. Phage particles bound to the target were eluted and used to infect TG1 cells. Infected cells (10 µL) from each treatment were plated on LB/CB plates (FIG. 7A). As seen in FIG. 5, the higher the temperature applied before the selection process, the greater is the reduction in the number of colonies, confirming that high temperature is an effective negative, selective pressure on the displayed protein domain. A quantitative assessment of the number of colonies isolated after each heat treatment can easily be determined by plating (FIG. 7B).

Example 19

Testing Output Clones by Phage ELISA

Phage particles produced from 96 clones isolated after round #3, were heated at 50° C. for 3 hr and cooled to RT. The phage supernatants were then incubated with both the target peptide (500 ng/well) immobilized on NeutrAvidin (1 µg/well) coated plate wells and an unrelated target (background). Binding phage clones were detected using anti-M13 antibody conjugated to HRP (GE Healthcare). The green, colored product of the enzymatic reaction in the microtiter plate wells was measured at 405 nm using the FLUOstar OPTIMA plate reader (BMG Labtech). Wells that generated signals on the target plate but not on the background plate (FIG. 9A), suggest that those phage clones represent potential binders for the target. In some cases, the signal over background ratio ranged from 3 to 20 for clones (FIG. 9B).

Example 20

Figure 10:
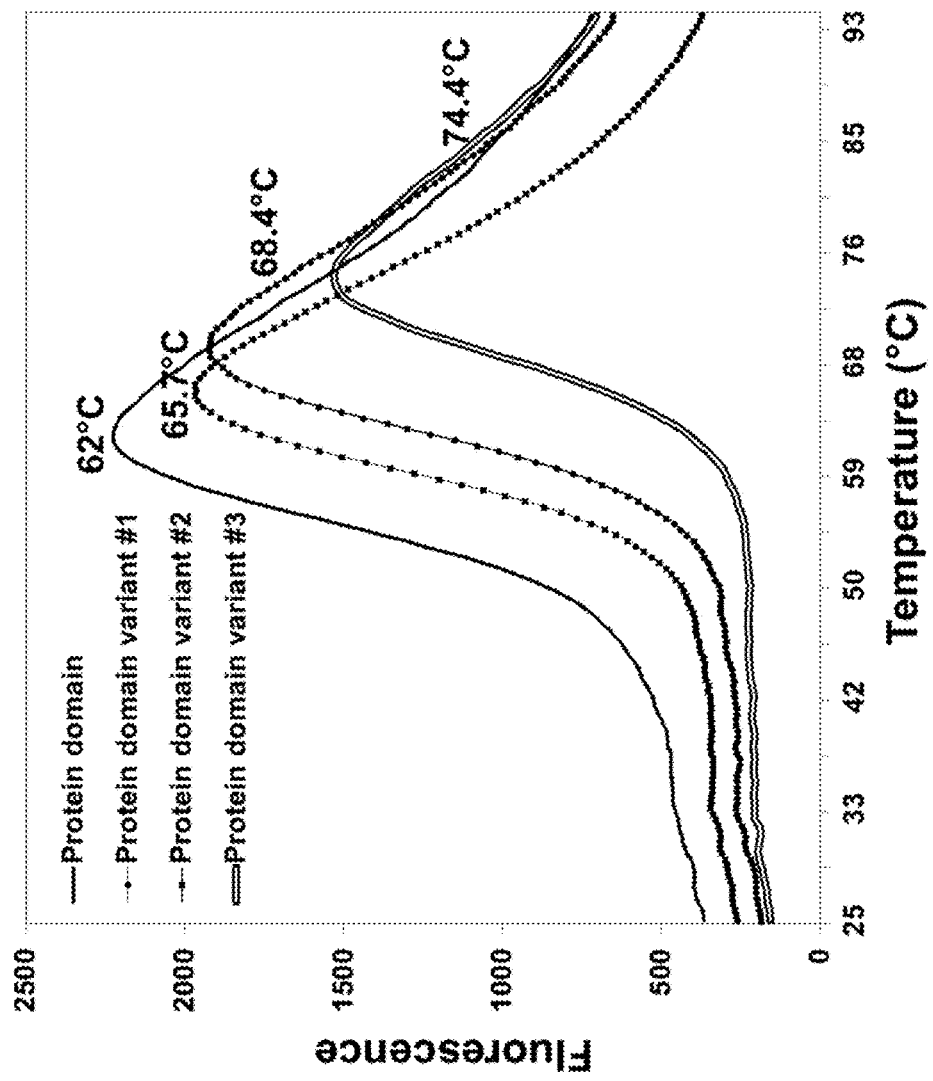
FIG. 10 is a graph of thermal melting temperatures of wild-type domain and three variants. Purified protein domains were heated from 25° C. through 95° C. in the presence of the fluorescent dye, SYPRO orange. Protein unfolding was accompanied by increase in dye fluorescence, which is plotted on the Y-axis as a function of temperature on the X-axis. The melting temperature ($T_m$) values are indicated as the temperature at which the maximum fluorescent signal was generated.

Determining the Melting Temperature $T_m$ of the Thermally Stable Variants by a Fluorescence-Based Thermal Shift Assay The $T_m$ (temperature at which 50% of the protein is unfolded) of the protein domain variants was determined by a fluorescence-based thermal shift assay (Giuliani et al. (2008) *Biochemistry* 47, 13974-84). The proteins were mixed with SYPRO orange dye, and heated from 25° C. to 95° C. on a real-time thermocycler. SYPRO orange dye interacts with a protein undergoing thermal unfolding, with its fluorescence increasing upon exposure to the protein's hydrophobic core. The melting curves of four protein domains are represented in FIG. 10, with fluorescence intensity represented on V-axis as a function of temperature on X-axis. The $T_m$ value is indicated as the temperature at the highest fluorescent intensity of the curve. The starting protein domain has a $T_m$ of 62° C., whereas, the three protein domain variants, which were selected from the mutagenic library by applying high temperature as the selective pressure, have increased $T_m$ values of 65.7° C., 68.4° C., and 74.4° C.

What is claimed is:

1. A polypeptide comprising a FHA domain variant derived from the wild-type FHA1 domain of *Saccharomyces cerevisiae* Rad53 (Rad53) (SEQ ID NO:7), comprising an amino acid sequence having at least one amino acid sequence change that increases specific binding of the polypeptide to a peptide or polypeptide comprising a phosphothreonine residue, wherein the amino acid sequence change is in a position, relative to the wild-type FHA1 domain of Rad53, that is S34, N121, W66, Q25, S13, I104, or R164.

2. The polypeptide of claim 1, wherein the amino acid sequence change is position S34 and wherein the mutation substitutes for serine an amino acid that is a hydrophobic mutation.

3. The polypeptide of claim 2, wherein the amino acid sequence change is S34F, S34A, S34M, S34I, S34L, S34Y, or S34V.

4. A polypeptide comprising a FHA domain variant derived from the wild-type FHA1 domain of *Saccharomyces cerevisiae* Rad53 (Rad53) (SEQ ID NO:7), comprising an amino acid sequence having at least one amino acid sequence change that increases specific binding of the polypeptide to a peptide or polypeptide comprising a phosphothreonine residue, wherein the variant comprising at least one amino acid sequence change in a position that is N121, L141, T15, L48, Q16, T39, K59, C74, G94, S11, A14, S82, E129, or N158, the mutation correlated with increased thermostability relative to a polypeptide comprising a FHA1 domain of Rad53 lacking the mutation.

5. The polypeptide of claim 4, wherein the mutation is N121Y, L141I, T15A, L48F, Q16R, T39P, K59E, C74S, G94D, S11T, A14V, S82R, E129V, or N158I.

* * * * *